US010703751B2

(12) United States Patent
Larsen et al.

(10) Patent No.: US 10,703,751 B2
(45) Date of Patent: Jul. 7, 2020

(54) AMINO-IMIDAZOPYRIDINE DERIVATIVES AS JANUS KINASE INHIBITORS AND PHARMACEUTICAL USE THEREOF

(71) Applicant: LEO Pharma A/S, Ballerup (DK)

(72) Inventors: Jens Larsen, Ballerup (DK); Mogens Larsen, Ballerup (GB); Lars Kyhn Rasmussen, Vanløse (DK); Andreas Ritzen, Ballerup (DK); Tine Marianne Duus, Ballerup (DK)

(73) Assignee: Leo Pharma A/S, Ballerup (DK)

(*) Notice: Subject to any disclaimer, the term of this patent is extended or adjusted under 35 U.S.C. 154(b) by 0 days.

(21) Appl. No.: 16/477,249

(22) PCT Filed: Jan. 10, 2018

(86) PCT No.: PCT/EP2018/050548
§ 371 (c)(1),
(2) Date: Jul. 11, 2019

(87) PCT Pub. No.: WO2018/130563
PCT Pub. Date: Jul. 19, 2018

(65) Prior Publication Data

US 2019/0367512 A1 Dec. 5, 2019

(30) Foreign Application Priority Data

Jan. 11, 2017 (EP) .................................... 17151020

(51) Int. Cl.
*C07D 471/04* (2006.01)
*A61K 45/06* (2006.01)

(52) U.S. Cl.
CPC ............ *C07D 471/04* (2013.01); *A61K 45/06* (2013.01)

(58) Field of Classification Search
CPC .............................. C07D 471/04; A61K 45/06
See application file for complete search history.

(56) References Cited

FOREIGN PATENT DOCUMENTS

| | | | |
|---|---|---|---|
| EP | 2518071 A1 | 10/2012 |
| WO | WO 2011/086053 A1 | 7/2011 |
| WO | WO 2013/007765 A1 | 1/2013 |
| WO | WO 2013/007768 A1 | 1/2013 |
| WO | WO 2014/071031 A1 | 5/2014 |
| WO | WO 2018/067422 A1 | 4/2018 |
| WO | WO 2018/112382 A1 | 6/2018 |

OTHER PUBLICATIONS

Zak, M et al. "Identification of C-2 Hydroxyethyl Imidazopyrrolopyridines as Potent JAK1 Inhibitors with Physicochemical Properties and High Selectivity over JAK2," Journal of Medicinal Chemistry, 2013, 56 pp. 4764-4785.
O'Shea, J.J., "Targeting the Jak/STAT pathway for immunosuppression," Ann. Rheum. Dis., vol. 63 (Suppl. 2:ii67-ii71) (5 pages), (2004).
O'Shea, John J., M.D., "JAKs and STATs in Immunity, Immunodeficiency, and Cancer," The New England Journal of Medicine, vol. 368, No. 2, pp. 161-170 (2013).
O'Shea, John J. et al., "Cytokine Signaling in 2002: New Surprises in the Jak/Stat Pathway," Cell., vol. 109, pp. S121-S131 (2002).
Schindler, Christian W., "Series Introduction: JAK-STAT signaling in human disease," J. Clin. Invest., vol. 109, No. 9, pp. 1133-1137 (2002).
Schindler, Christian et al., "JAK-STAT Signaling: From Interferons to Cytokines," Journal of BIological Chemistry, vol. 282, No. 28, pp. 20059-20063 (2007).
Schartz, Daniella M. et al., "Type I/II cytokines, JAKs, and new strategies for treating autoimmune diseases," Nat. Rev. Rheumatol., vol. 12, No. 1, pp. 25-36 (2016).
International Search Report for International Application No. PCT/EP2018/050548, dated Apr. 20, 2018. (2 pages).
Written Opinion of the International Searching Authority for International Application No. PCT/EP2018/050548. (7 pages).

*Primary Examiner* — John M Mauro
(74) *Attorney, Agent, or Firm* — Finnegan, Henderson, Farabow, Garrett & Dunner, LLP

(57) ABSTRACT

The present invention relates to a compound according to formula (I)

(I)

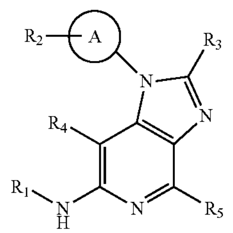

or pharmaceutically acceptable salts, hydrates, or solvates thereof; wherein $R_1$ is $C_1$-alkyl, $R_2$ is $C_1$-alkyl, $R_3$ is $C_2$-alkyl, $R_4$ is hydrogen, $R_5$ is hydrogen. The invention relates further to said compounds for use in therapy, to pharmaceutical compositions comprising said compounds, to said compounds for use in the treatment autoimmune diseases and to intermediates for the preparation of said compounds.

14 Claims, No Drawings

AMINO-IMIDAZOPYRIDINE DERIVATIVES AS JANUS KINASE INHIBITORS AND PHARMACEUTICAL USE THEREOF

This application is a national stage filing under 35 U.S.C. § 371 of International Application No. PCT/EP2018/050548, filed on Jan. 10, 2018, which claims priority of European Patent Application No. 17151020.9, filed on Jan. 11, 2017. The contents of these applications are each incorporated herein by reference.

FIELD OF THE INVENTION

This invention relates to compounds which are inhibitors of Janus kinases and derivatives thereof, to intermediates for the preparation of said compounds, to said compounds for use in therapy and to pharmaceutical compositions comprising said compounds.

BACKGROUND OF THE INVENTION

This invention relates to novel compounds which are inhibitors of protein tyrosine kinases such as the Janus kinases (JAK1, JAK2, JAK3 and TYK2) and in particular Janus kinase 1 (JAK1).

Protein tyrosine kinases are a family of enzymes catalyzing the transfer of the terminal phosphate of adenosine triphosphate to tyrosine residues in protein substrates. Phosphorylation of tyrosine residues on protein substrates leads to transduction of intracellular signals which regulate a wide variety of processes such as cell growth differentiation and activation, metabolism, hematopoiesis, host defense and immuno-regulation. As the elucidation of the molecular mechanisms in a number of inflammatory conditions and other disorders of the immune system (e.g. autoimmune diseases), highlighted the critical role of these intracellular signal pathways, modulation of the activity of protein tyrosine kinases appears to be an attractive route to the management of inflammatory diseases. A large number of protein tyrosine kinases have been identified which may be receptor protein tyrosine kinases, e.g. the insulin receptor, or non-receptor protein tyrosine kinases.

The protein tyrosine kinases JAK1, JAK2, JAK3 and TYK2 selectively associate with the cytoplasmic domains of various cytokine receptor chains and have essential roles in cytokine-dependent regulation of tissue homeostasis, initiation of innate immunity, shaping adaptive immune responses and inflammatory processes. They are critical in signal transduction in response to their activation via tyrosine phosphorylation by stimulation of cytokine receptors. (1) Schindler C. et al. JAK-STAT signaling: from interferons to cytokines. J. Biol. Chem 2007; 282(28):20059; (2) O'Shea J. J. Targeting the Jak/STAT pathway for immunosuppression; Ann. Rheum. Dis. 2004; 63 Suppl 2:ii67; (3) Schindler C. Series introduction. JAK-STAT signaling in human disease; J. Clin. Invest. 2002; 109(9):1133); (4) O'Shea et. Al. Cell, Vol. 109, S121-S131, 2002; (5) Schwartz D. M. et al. Nat. Rev. Rheumatol., 2016; 12(1): 25-36; (6) O'Shea et al. New. Eng. J. Med. 2013; 368(2): 161-170.

While JAK1, JAK2 and TYK2 are ubiquitously expressed JAK3 is predominantly expressed in hematopoietic cells.

JAK1 plays a critical role in mediation of biological responses and JAK1 is widely expressed and associated with several major cytokine receptor families. It is involved in signaling by members of the IL-2 receptor γ subunit family (IL-2, IL-4, IL-7R, IL-9R, IL-15R and IL-21R), the IL-4 receptor family (IL-4R, IL-13R), the gp130 receptor family and class II cytokine receptors comprising of IL-10 receptor family and both type I and type II IFN receptor family.

JAK2 is implicated in signaling by several single chain receptors (including Epo-R, GHR, PRL-R), the IL-3 receptor family, the gp130 receptor family, the IL-12 receptor family (IL-12 and IL-23) and some Class II receptor cytokine family. Thus, JAK2 plays a critical role in transducing signals for Epo, IL-3, GM-CSF, IL-5 and IFNγ. JAK2 knockout mice exhibit an embryonic lethal phenotype.

JAK3 is involved in signal transduction by receptors that employ the common gamma chain of the type I cytokine receptor family also known as IL-2 receptor family (e.g. IL-2, IL-4, IL-7, IL-9, IL-15 and IL-21). XSCID patient populations have been identified with reduced levels of JAK3 protein or with genetic defects to the common gamma chain, suggesting that immune suppression should result from blocking signaling through the JAK3 pathway. Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as immune system diseases, in particular autoimmune diseases.

TYK2 is implicated in type I interferons, IL-6, IL-10, IL-12 and IL-23 signaling. A human patient with a TYK2 deficiency has been described and this patient had a primary immunodeficiency disorder characterized as a hyper-IgE-like syndrome with many opportunistic infections by virus, bacteria and fungi. Because IL-23 has been found to play an important role in many chronic inflammatory conditions, a TYK2 inhibitor could conceivably be very effective in treating diseased influenced by IL-23.

Anemia and neutropenia may be related to inhibition of EPO and GM-CSF respectively, since the biological effect by these two cytokines apparently depends exclusively on JAK2 activation. Similarly, IL-12 and IL-23 are involved in engaging innate and adaptive immune defense to viruses, bacteria, and fungi. Because these cytokines bind to receptors that recruit JAK2 and TYK2 in their signaling cascade it is conceivable that a selective JAK1 inhibitor will not affect their biological activity and thus have a safer profile compared to compounds which inhibit JAK1, JAK2, JAK3 and TYK2.

Activation of JAK lead to the activation of STAT molecules and thus to the elicitation of JAK/STAT signaling pathway, which is highly regulated by phosphorylation events. Activation of STAT molecules is considered a valid pharmaco-dynamic marker for JAK activity and the activity of specific JAK molecules can be assessed by the level of preferential recruited active STAT molecule.

In particular, the receptor of IL-4 expressed by immune cells is constituted by two different chains, the ligand high affinity and signal transducer IL-4Ra and common-γ chain, activating JAK1 and JAK3 respectively upon ligand binding, which leads to the recruitment and activation of STAT6. Similarly, the IL-6 receptor is a heterodimer receptor formed by the IL-6 high affinity receptor chain (IL-6Ra) and the signal transducer glycoprotein 130 (gp130) chain to which JAK1 preferentially associates. The gp130 chain activates JAK1 and STAT3 signaling pathway upon ligand binding. Therefore, to investigate the activity of JAK1, the level of active STAT6 or STAT3 can be assessed in immune cells after stimulation with either IL-4 or IL-6, respectively.

Furthermore, the receptor for erythropoietin (EPOR) is a homodimer receptor constituted by two identical receptor chains. Therefore, the EPOR chain is both high affinity ligand binding and signal transducer chain and activates only the associated JAK2 molecule upon ligand binding, leading to the recruitment and activation of STAT5. Receptor for GM-CSF is a heterodimer receptor constituted by the GM-CSF high affinity receptor chain (GM-CSFR$\alpha$) and the signal transducer chain (GM-CSFR$\beta$), to which JAK2 specifically associates. Upon ligand binding, association of $\alpha$ and $\beta$ receptor chains results in the activation of JAK2 and STAT5 signaling pathway. Therefore, to investigate the activity of JAK2, the level of active STAT5 can be assessed in immune cells after stimulation with either GM-CSF or erythropoietin (EPO).

Inhibitors of the Janus kinases are expected to show utility in the treatment of inflammatory and non-infectious autoimmune diseases wherein these kinases are involved. Recently the pan-JAK inhibitors tofacitinib and ruxolitinib have been launched for the treatment of rheumatoid arthritis and myelofibrosis, respectively. JAK1 inhibitor PF-04965842 is presently in phase III clinical trials for the treatment of atopic dermatitis, JAK1 inhibitor baricitinib has been launched for the treatment of rheumatoid arthritis and is in phase III trials for the treatment of atopic dermatitis and JAK1 inhibitor upadacitinib is presently in phase III clinical trials for the treatment of rheumatoid arthritis and psoriatic arthritis and in phase II trials for the treatment of atopic dermatitis, Crohn's disease and ulcerative colitis.

Hence, JAK inhibitors may furthermore be useful in the treatment of diseases related to activity of Janus kinases, including, for example skin diseases like psoriasis, atopic dermatitis, scleroderma, rosacea, skin cancers, dermatitis, dermatitis herpetiformis, dermatomyositis, vitiligo, alopecia areata, contact dermatitis, eczema, xerosis, ichthyosis, urticaria, chronic idiophatic pruritus, pyoderma gangrenosum, cutaneous lupus erythematosus and lichen planus; respiratory diseases like asthma, chronic obstructive pulmonary disease, pulmonary fibrosis, cystic fibrosis, rhinitis, bronchiolitis, byssinosis, pneumoconiosis, bronchiectasis, hypersensitivity pneumonitis, lung cancers, mesothelioma and sarcoidosis; gastrointestinal diseases like inflammatory bowel disease, ulcerative colitis, Crohn's disease, retroperitoneal fibrosis, celiac disease and cancers; eye diseases like myasthenia gravis, Sjögren's syndrome, conjunctivitis, scleritis, uveitis, dry eye syndrome, keratitis, iritis; systemic indications like lupus, multiple sclerosis, rheumatoid arthritis, type I diabetes and complications from diabetes, cancers, ankylosing spondylitis and psoriatic arthritis; cancer like bone and soft tissue tumors, head-neck cancer as well as other autoimmune diseases and indications where immunosuppression would be desirable for example in organ transplantation.

WO2013007768 discloses Tricyclic Heterocyclic Compounds, Compositions and Methods of use thereof as JAK Inhibitors.

WO2013007765 discloses Fused Tricyclic Compounds for use as Inhibitors of Janus Kinases.

WO2011086053 discloses Tricyclic Heterocyclic Compounds, Compositions and Methods of use thereof.

Zak, M. et. Al, *J. Med. Chem.*, (2013), 56, 4764-85, discloses imidazopyrrolopyridines as JAK1 inhibitors.

There remains a need for new compounds which effectively and selectively inhibit specific JAK enzymes, in particular inhibitors which selectively inhibit JAK1 vs. JAK2 to reduce adverse effects without affecting the overall anti-inflammatory efficacy.

SUMMARY OF THE INVENTION

Compounds of the present invention exhibit inhibitory activity on the Janus kinases; and in particular compounds of the invention exhibit inhibitory activity on JAK1. Thus compounds of the present invention show JAK kinase inhibitory selectivity; particularly the compounds show inhibitory selectivity of JAK1 vs. JAK2. It follows that compounds of the present invention may also show inhibitory selectivity of STAT6 or STAT3 vs. STAT5.

Some compounds of the present invention have particularly favourable pharmacokinetic properties for systemic use, such as high metabolic stability and high aqueous solubility.

Some compounds of the present invention have particularly favourable toxicological properties such as high kinase as well as general off target selectivity, no CYP inhibition, low or no CYP induction, low cytotoxicity; as well as being well tolerated in repeated dose toxicological studies.

Accordingly, the present invention relates to a compound according to formula (I)

(I)

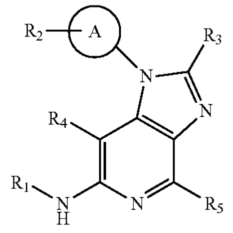

wherein

A represents $C_6$-cycloalkyl, wherein said $C_6$-cycloalkyl is optionally substituted with one or more deuterium;

$R_1$ represents $C_1$-alkyl, wherein said $C_1$-alkyl is optionally substituted with one or more deuterium;

$R_2$ represents $C_1$-alkyl, wherein said $C_1$-alkyl is substituted with a substituent selected from $R_6$; and wherein said $C_1$-alkyl is optionally substituted with one or more deuterium;

$R_3$ represents $C_2$-alkyl, wherein said $C_2$-alkyl is substituted with a substituent selected from $R_7$ and wherein said $C_2$-alkyl is optionally substituted with one or more deuterium;

$R_4$ represents hydrogen or deuterium;

$R_5$ represents hydrogen or deuterium;

$R_6$ represents cyano;

$R_7$ represents hydroxyl;

or pharmaceutically acceptable salts, hydrates or solvates thereof.

In another aspect, the invention relates to a pharmaceutical composition comprising a compound of general formula (I) as defined herein together with a pharmaceutically acceptable vehicle or excipient or pharmaceutically acceptable carrier(s), optionally together with one or more other therapeutically active compound(s).

In yet another aspect, the invention relates to a compound according to general formula (I) as defined herein for use as a medicament.

In yet another aspect, the invention relates to a compound according to general formula (I) as defined herein for use in the prophylaxis and/or treatment of diseases of the immune system such as autoimmune diseases, or of diseases related to deregulation of the immune system.

In yet another aspect the invention relates to intermediates useful in the preparation of compounds of general formula (I).

DETAILED DESCRIPTION OF THE INVENTION

Definitions

The term "$C_a$-alkyl" is intended to indicate a radical obtained when one hydrogen atom is removed from a branched or linear hydrocarbon. Said alkyl comprises 1-2 carbon atoms, such as methyl and ethyl The number of carbon atoms in "alkyl" is indicated by the prefix "$C_a$", wherein a is the number carbons in the hydrocarbon radical. Thus, $C_1$-alkyl is intended to indicate an alkyl radical comprising 1 carbon atom, i.e. methyl. $C_2$-alkyl is intended to indicate an alkyl radical comprising 2 carbon atoms, i.e. ethyl.

The term "cyano" is intended to indicate a —CN group attached to the parent molecular moiety through the carbon atom.

The term "$C_6$-cycloalkyl" is intended to indicate a saturated cycloalkane hydrocarbon radical, comprising 6 carbon atoms, i.e. cyclohexyl.

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-10 carbon atoms, and preferably comprises 1-6, e.g. 1-4, e.g. 1-3, e.g. 1-2, e.g. 6 carbon atoms. The term includes alkyl and cycloalkyl, as indicated herein.

The terms "hydroxy" or "hydroxyl" are intended to indicate an —OH group.

BrettPhos is intended to indicate 2-(Dicyclohexylphosphino)3,6-dimethoxy-2',4',6'-triisopropyl-1,1'-biphenyl.

tBuBrettPhos is intended to indicate 2-(Di-tert-butylphosphino)-2',4',6'-triisopropyl-3,6-dimethoxy-1,1'-biphenyl.

tBuXPhos is intended to indicate 2-Di-tert-butylphosphino-2',4',6'-triisopropylbiphenyl.

BrettPhos Pd G1 is intended to indicate Chloro[2-(dicyclohexylphosphino)-3,6-dimethoxy-2',4',6'-triisopropyl-1,1'-biphenyl][2-(2-aminoethyl)phenyl]palladium(II.

BrettPhos Pd G3 is intended to indicate [(2-Di-cyclohexylphosphino-3,6-dimethoxy-2',4',6'-triisopropyl-1,1'-biphenyl)-2-(2'-amino-1,1'-biphenyl)]palladium(II) methanesulfonate.

tBuBrettPhos Pd G3 is intended to indicate [(2-Di-tert-butylphosphino-3,6-dimethoxy-2',4',6'-triisopropyl-1,1'-biphenyl)-2-(2'-amino-1,1'-biphenyl)]palladium(II) methanesulfonate, tBuXPhos Pd G1 is intended to indicate [2-(Di-tert-butylphosphino)-2',4',6'-triisopropyl-1,1'-biphenyl][2-(2-aminoethyl)phenyl)]palladium(II) chloride.

tBuXPhos Pd G3 is intended to indicate [(2-Di-tert-butylphosphino-2',4',6'-triisopropyl-1,1'-biphenyl)-2-(2'-amino-1,1'-biphenyl)] palladium(II) methanesulfonate.

If substituents are described as being independently selected from a group, each substituent is selected independent of the other. Each substituent may therefore be identical or different from the other substituent(s).

The term "optionally substituted" means "unsubstituted or substituted", and therefore the general formulas described herein encompasses compounds containing the specified optional substituent(s) as well as compounds that do not contain the optional substituent(s).

The term "pharmaceutically acceptable salt" is intended to indicate salts prepared by reacting a compound of formula (I), which comprise a basic moiety, with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic, fumaric acid, aceturic, L-lactic, glycolic, oxalic, saccharic, DL-mandelic or L-tartaric. Further examples of pharmaceutical acceptable salts are listed in Berge, S. M.; J. Pharm. Sci.; (1977), 66(1), 1-19, which is incorporated herein by reference.

The term "solvate" is intended to indicate a species formed by interaction between a compound, e.g. a compound of formula (I), and a solvent, e.g. alcohol, glycerol, dioxane or water, wherein said species are in a crystalline form or in an amorphous form. When water is the solvent, said species is referred to as a hydrate.

The term "treatment" as used herein means the management and care of a patient for the purpose of combating a disease, disorder or condition. The term is intended to include the delaying of the progression of the disease, disorder or condition, the amelioration, alleviation or relief of symptoms and complications, and/or the cure or elimination of the disease, disorder or condition. The term also include prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

All references, including publications, patent applications and patents, cited herein are hereby incorporated by reference in their entirety and to the same extent as if each reference were individually and specifically indicated to be incorporated by reference, regardless of any separately provided incorporation of particular documents made elsewhere herein.

EMBODIMENTS OF THE INVENTION

In an embodiment the invention provides a compound of general formula (I) wherein formula (I) is general formula (Ia)

(Ia)

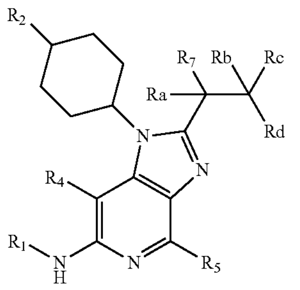

Wherein $R_1$-$R_2$, $R_4$-$R_7$ are as defined above and wherein Ra, Rb, Rc and Rd each independently are selected from hydrogen and deuterium;

or pharmaceutically acceptable salts, hydrates or solvates thereof.

In an embodiment the invention provides a compound of general formula (I); wherein formula (I) is general formula (Ib)

(Ib)

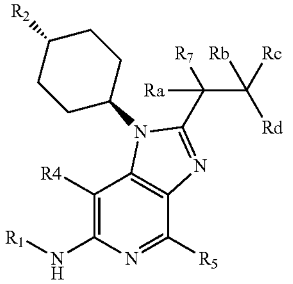

Wherein $R_1$-$R_2$, $R_4$-$R_7$ are as defined above and wherein Ra, Rb, Rc and Rd each independently are selected from hydrogen and deuterium;

or pharmaceutically acceptable salts, hydrates or solvates thereof.

In an embodiment the invention provides a compound of general formula (I); wherein formula (I) is general formula (Ic)

(Ic)

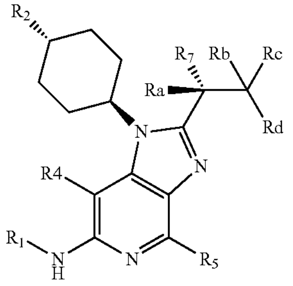

Wherein $R_1$-$R_2$, $R_4$-$R_7$ are as defined above and wherein Ra, Rb, Rc and Rd each independently are selected from hydrogen and deuterium;

or pharmaceutically acceptable salts, hydrates or solvates thereof.

In an embodiment the invention provides a compound of general formula (I); wherein formula (I) is general formula (Id)

(Id)

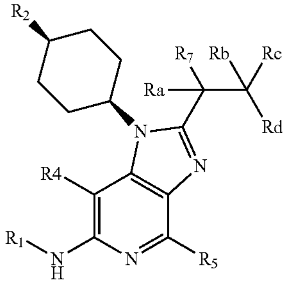

Wherein $R_1$-$R_2$, $R_4$-$R_7$ are as defined above and wherein Ra, Rb, Rc and Rd each independently are selected from hydrogen and deuterium;

or pharmaceutically acceptable salts, hydrates or solvates thereof.

In an embodiment the invention provides a compound of general formula (I) as defined herein; wherein A represents $C_6$-cycloalkyl; $R_1$ represents $C_1$-alkyl; $R_2$ represents $C_1$-alkyl, wherein said $C_1$-alkyl is substituted with a substituent selected from $R_6$; $R_3$ represents $C_2$-alkyl, wherein said $C_2$-alkyl is substituted with a substituent selected from $R_7$; $R_4$ represents hydrogen; $R_5$ represents hydrogen; $R_6$ represents cyano; $R_7$ represents hydroxyl; or pharmaceutically acceptable salts, hydrates or solvates thereof.

In an embodiment the invention provides a compound of general formula (I) as defined herein; wherein A represents $C_6$-cycloalkyl; $R_1$ represents $C_1$-alkyl optionally substituted with one or more deuterium; $R_2$ represents $C_1$-alkyl, wherein said $C_1$-alkyl is substituted with a substituent selected from $R_6$; $R_3$ represents $C_2$-alkyl, wherein said $C_2$-alkyl is substituted with a substituent selected from $R_7$; $R_4$ represents hydrogen; $R_5$ represents hydrogen; $R_6$ represents cyano; $R_7$ represents hydroxyl;

or pharmaceutically acceptable salts, hydrates or solvates thereof.

Any combination of two or more embodiments described herein is considered within the scope of the present invention.

The present invention includes all embodiments wherein $R_1$, $R_2$, $R_3$, $R_4$, $R_5$, $R_6$ and $R_7$ are combined in any combination as anywhere described herein.

In an embodiment the invention provides a compound of general formula (I) as defined herein; the compound being selected from selected from trans-2-[4-[2-[1-Hydroxyethyl]-6-(methylamino)imidazo[4,5-c]pyridin-1-yl]cyclohexyl]acetonitrile, trans-2-[4-[2-[(1S)-1-Hydroxyethyl]-6-(methylamino)imidazo[4,5-c]pyridin-1-yl]cyclo-hexyl]acetonitrile, trans-2-[4-[2-[(1R)-1-Hydroxyethyl]-6-(methylamino)imidazo[4,5-c]pyridin-1-yl]cyclohexyl]acetonitrile, trans-2-[4-[2-[(1R)-1-Hydroxyethyl]-6-(trideuteriomethylamino)imidazo[4,5-c]pyridin-1-yl]cyclohexyl]acetonitrile, trans-2-[4-[2-[1,2,2,2-Tetradeuterio-1-hydroxyethyl]-6-(methylamino)imidazo[4,5-c]pyridin-1-yl]cyclohexyl]acetonitrile, cis-2-[4-[2-[1-Hydroxyethyl]-6-(methylamino)imidazo[4,5-c]pyridin-1-yl]cyclohexyl]acetonitrile and cis-2-[4-[2-[(1R)-1-Hydroxyethyl]-6-(methylamino)imidazo[4,5-c]pyridin-1-yl]cyclohexyl]acetonitrile, or pharmaceutically acceptable salts, hydrates or solvates thereof.

In an embodiment the invention provides a compound of general formula (I) as defined herein selected from trans-2-[4-[2-[1-Hydroxyethyl]-6-(methylamino)imidazo[4,5-c]pyridin-1-yl]cyclohexyl]acetonitrile, trans-2-[4-[2-[(1S)-1-Hydroxyethyl]-6-(methylamino)imidazo[4,5-c]pyridin-1-yl]cyclo-hexyl]acetonitrile and trans-2-[4-[2-[(1R)-1-Hydroxyethyl]-6-(methylamino)imidazo[4,5-c]pyridin-1-yl]cyclohexyl]acetonitrile, or pharmaceutically acceptable salts, hydrates or solvates thereof.

In an embodiment the invention provides a compound of general formula (I) as defined herein selected from a deuterated form of trans-2-[4-[2-[1-Hydroxyethyl]-6-(methylamino)imidazo[4,5-c]pyridin-1-yl]cyclohexyl]acetonitrile, trans-2-[4-[2-[(1S)-1-Hydroxyethyl]-6-(methylamino)imidazo[4,5-c]pyridin-1-yl]cyclo-hexyl]acetonitrile and trans-2-[4-[2-[(1R)-1-Hydroxyethyl]-6-(methylamino)imidazo[4,5-c]pyridin-1-yl]cyclohexyl]acetonitrile, or pharmaceutically acceptable salts, hydrates or solvates thereof.

An embodiment of the invention provides a compound of formula (I), said compound being trans-2-[4-[2-[1-Hydroxyethyl]-6-(methylamino)imidazo[4,5-c]pyridin-1-yl]cyclohexyl]acetonitrile, or pharmaceutically acceptable salts, hydrates or solvates thereof.

An embodiment of the invention provides a compound of formula (I), said compound being trans-2-[4-[2-[(1S)-1-Hydroxyethyl]-6-(methylamino)imidazo[4,5-c]pyridin-1-yl]cyclohexyl]acetonitrile or pharmaceutically acceptable salts, hydrates or solvates thereof.

An embodiment the invention provides a compound of formula (I), said compound being trans-2-[4-[2-[(1R)-1-Hydroxyethyl]-6-(methylamino)imidazo[4,5-c]pyridin-1-yl]cyclohexyl]acetonitrile or pharmaceutically acceptable salts, hydrates or solvates thereof.

An embodiment the invention provides a compound of formula (I), said compound being trans-2-[4-[2-[(1R)-1-Hydroxyethyl]-6-(trideuteriomethylamino)imidazo[4,5-c]pyridin-1-yl]cyclohexyl]acetonitrile or pharmaceutically acceptable salts, hydrates or solvates thereof.

An embodiment the invention provides a compound of formula (I), said compound being trans-2-[4-[2-[1,2,2,2-Tetradeuterio-1-hydroxyethyl]-6-(methylamino)imidazo[4,5-c]pyridin-1-yl]cyclohexyl]acetonitrile or pharmaceutically acceptable salts, hydrates or solvates thereof.

An embodiment the invention provides a compound of formula (I), said compound being cis-2-[4-[2-[1-Hydroxyethyl]-6-(methylamino)imidazo[4,5-c]pyridin-1-yl]cyclohexyl]acetonitrile or pharmaceutically acceptable salts, hydrates or solvates thereof.

An embodiment the invention provides a compound of formula (I), said compound being cis-2-[4-[2-[(1R)-1-Hydroxyethyl]-6-(methylamino)imidazo[4,5-c]pyridin-1-yl]cyclohexyl]acetonitrile, or pharmaceutically acceptable salts, hydrates or solvates thereof.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile, or pharmaceutically acceptable salts thereof.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile, or hydrates thereof.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile, or solvates thereof.

In an embodiment the invention provides a compound of general formula (I); wherein said compound is a deuterated form of trans-2-[4-[2-[(1R)-1-Hydroxyethyl]-6-(methylamino)imidazo[4,5-c]pyridin-1-yl]cyclohexyl]acetonitrile.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile malonic acid salt.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile glycolic acid salt.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile L-tartaric acid salt.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile L-malic acid salt.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile sulfuric acid salt.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile hydrochloric acid salt.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile succinic acid salt.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile oxalic acid salt.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile fumaric acid salt.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile 1,5-naphthalenedisulfonic acid salt.

In an embodiment the invention provides a compound of general formula (I); wherein said compound is trans-2-[4-[2-[(1R)-1-Hydroxyethyl]-6-(methylamino)imidazo[4,5-c]pyridin-1-yl]cyclohexyl]acetonitrile DL-mandelic acid salt.

In one or more embodiments the invention provides intermediates of general formula (II)

(II)

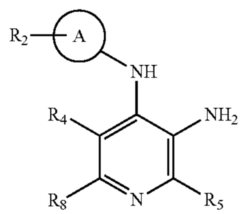

wherein

A represents $C_6$-cycloalkyl;

$R_2$ represents $C_1$-alkyl, wherein said $C_1$-alkyl is substituted with a substituent selected from $R_6$; and wherein said $C_1$-alkyl is optionally substituted with one or more deuterium;

$R_4$ represents hydrogen or deuterium;

$R_5$ represents hydrogen or deuterium;

$R_6$ represents cyano;

$R_8$ represents halogen;

or salts thereof;

useful for the preparation of compounds of general formula (I).

In an embodiment the invention provides intermediates selected from

2-[trans-4-[(5-Amino-2-chloropyridin-4-yl)amino]cyclohexyl]acetonitrile and salts thereof.

In one or more embodiments the invention provides intermediates of general formula (III)

(III)

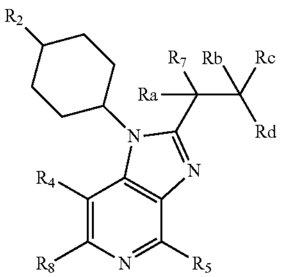

Wherein $R_2$ represents $C_1$-alkyl, wherein said $C_1$-alkyl is substituted with a substituent selected from $R_6$; and wherein said $C_1$-alkyl is optionally substituted with one or more deuterium;

$R_4$ represents hydrogen or deuterium;

$R_5$ represents hydrogen or deuterium;

$R_6$ represents cyano;

$R_7$ represents hydroxyl;

Ra, Rb, Rc and Rd each independently are selected from hydrogen and deuterium;

$R_8$ represents halogen;

or salts thereof;

useful for the preparation of compounds of general formula (Ia).

In an embodiment the invention provides intermediates selected from

2-[trans-4-[6-Chloro-2-(1-hydroxyethyl)-1H-imidazo[4,5-c]pyridin-1-yl]cyclohexyl]-acetonitrile, 2-[trans-4-[6-Chloro-2-[(1R)-1-hydroxyethyl]-1H-imidazo[4,5-c]pyridin-1-yl]cyclohexyl]acetonitrile and trans-2-[4-[6-Chloro-2-(1,2,2,2-tetradeuterio-1-hydroxyethyl)imidazo[4,5-c]pyridin-1-yl]cyclohexyl]acetonitrile or salts thereof.

In an embodiment the invention relates to a process for the preparation of compound (Ia) from compound (III) comprising amination of compound (III) in the presence of a palladium catalyst, wherein $R_1$ represents $C_1$-alkyl, wherein said $C_1$-alkyl is optionally substituted with one or more deuterium;

$R_2$ represents $C_1$-alkyl, wherein said $C_1$-alkyl is substituted with a substituent selected from $R_6$; and wherein said $C_1$-alkyl is optionally substituted with one or more deuterium;

$R_4$ represents hydrogen or deuterium;

$R_5$ represents hydrogen or deuterium;

$R_6$ represents cyano;

$R_7$ represents hydroxyl;

Ra, Rb, Rc and Rd each independently are selected from hydrogen and deuterium $R_8$ represents halogen;

or salts thereof.

In an embodiment the invention relates to at process for the preparation of compound (Ia) from compound (III) comprising amination of compound (III) in the presence of a palladium catalyst, wherein the palladium catalyst comprises BrettPhos, tBuBrettPhos or tBuXPhos ligands.

In an embodiment the invention relates to at process for the preparation of compound (Ia) from compound (III) comprising amination of compound (III) in the presence of a palladium catalyst, wherein the palladium catalyst is selected from BrettPhos Pd G1, BrettPhos Pd G3, tBuBrettPhos Pd G3, tBuXPhos Pd G1 or tBuXPhos Pd G3.

In an embodiment the invention relates to at process for the preparation of compound (Ia) from compound (III) comprising amination of compound (III) in the presence of a palladium catalyst, wherein the palladium catalyst is prepared from a palladium source such as $PdCl_2$, $Pd_2(dba)_3$, or $Pd(OAc)_2$ in combination with BrettPhos, tBuBrettPhos or tBuXPhos ligands.

The compounds of formula (I) may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

Compounds of formula (I) comprise asymmetrically substituted (chiral) carbon atoms which give rise to the existence of isomeric forms, e.g. enantiomers and diastereomers.

The present invention relates to all such isomers, either in optically pure form or as mixtures thereof (e.g. racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. Preferably, if a specific stereoisomer is desired, said compound will be synthesized by stereoselective or stereospecific methods of preparation. These methods will advantageously employ chiral pure starting materials.

Furthermore, when a double bond or a fully or partially saturated ring system is present in the molecule geometric isomers may be formed. It is intended that any geometric isomer, as separated, pure or partially purified geometric isomers or mixtures thereof are included within the scope of the invention.

Di-substituted cycloalkanes, such as di-substituted cyclohexane may form geometric isomers; i.e. cis- and trans-isomers. Cis-isomers have both substituents on the same side of the ring, trans-isomers have the substituents on opposite sides of the ring. It is intended that any geometric isomer, as separated, pure or partially purified geometric isomers or mixtures thereof are included within the scope of the invention.

In the compounds of general formula (I), the atoms may exhibit their natural isotopic abundances, or one or more of the atoms may be artificially enriched in a particular isotope having the same atomic number, but an atomic mass or mass number different from the atomic mass or mass number found in nature. The present invention is meant to include all suitable isotopic variations of the compounds of general formula (I). For example, different isotopic forms of hydrogen include $^{1}H$, $^{2}H$ and $^{3}H$, different isotopic forms of carbon include $^{12}C$, $^{13}C$ and $^{14}C$ and different isotopic forms of nitrogen include $^{14}N$ and $^{15}N$. Enriching for deuterium ($^{2}H$) may for example increase in-vivo half-life or reduce dosage regiments, or may provide a compound useful as a standard for characterization of biological samples. Isotopically enriched compounds within general formula (I) can be prepared by conventional techniques well known to a person skilled in the art or by processes analogous to those described in the general procedures and examples herein using appropriate isotopically enriched reagents and/or intermediates.

In one or more embodiments of the present invention, the compounds of formula I as defined above are useful in therapy and in particular useful for treatment of for example skin diseases like proliferative and inflammatory skin disorders, psoriasis, atopic dermatitis, scleroderma, rosacea, skin cancers, dermatis, dermatitis herpetiformis, dermatomyositis, vitiligo, alopecia areata, contact dermatitis, eczema, xerosis, ichthyosis, urticaria, chronic idiophatic pruritus, pyoderma gangrenosum, cutaneous lupus erythematosus and lichen planus; respiratory diseases like asthma, chronic obstructive pulmonary disease, pulmonary fibrosis, cystic fibrosis, rhinitis, bronchiolitis, byssinosis, pneumoconiosis, bronchiectasis, hypersensitivity pneumonitis, lung cancers, mesothelioma and sarcoidosis; gastrointestinal diseases like inflammatory bowel disease, ulcerative colitis, Crohn's disease, retroperitoneal fibrosis, celiac disease and cancers; eye diseases like myasthenia gravis, Sjögren's syndrome, conjunctivitis, scleritis, uveitis, dry eye syndrome, keratitis, iritis; systemic indications like lupus, multiple sclerosis, rheumatoid arthritis, type I diabetes and complications from diabetes, cancers, ankylosing spondylitis and psoriatic arthritis; cancer like bone and soft tissue tumors, head-neck cancer, as well as other autoimmune diseases and indications where immunosuppression would be desirable for example in organ transplantation.

In an embodiment the invention provides compounds of formula I as defined above for use in the prophylaxis and/or treatment of psoriasis or atopic dermatitis.

In an embodiment the invention provides compounds of formula I as defined above for use in the prophylaxis and/or treatment of atopic dermatitis.

In an embodiment the invention provides a method of preventing, treating or ameliorating diseases of the immune system, such as autoimmune diseases, the method comprising administering to a person suffering from at least one of said diseases an effective amount of one or more compounds according to general formula I above optionally together with a pharmaceutically acceptable carrier or one or more excipients, optionally in combination with other therapeutically active compounds.

In an embodiment the invention provides a method of preventing, treating or ameliorating psoriasis or atopic dermatitis the method comprising administering to a person suffering from at least one of said diseases an effective amount of one or more compounds according to general formula I above optionally together with a pharmaceutically acceptable carrier or one or more excipients, optionally in combination with other therapeutically active compounds.

In an embodiment the invention provides a method of preventing, treating or ameliorating atopic dermatitis the method comprising administering to a person suffering from at least one of said diseases an effective amount of one or more compounds according to general formula I above optionally together with a pharmaceutically acceptable carrier or one or more excipients, optionally in combination with other therapeutically active compounds.

In an embodiment the invention provides a compound according to formula I for use in the manufacture of a medicament for the prophylaxis and/or treatment of diseases of the immune system, such as autoimmune disease, such as psoriasis or atopic dermatitis.

In an embodiment the invention provides a compound according to formula I for use in the manufacture of a medicament for the prophylaxis and/or treatment of diseases of the immune system, such as autoimmune disease, such as atopic dermatitis.

In one or more embodiments of the present invention, the compounds of formula I as defined above are useful as an anti-inflammatory agent capable of modulating the activity of a protein tyrosine kinase of the JAK family of protein tyrosine kinases, such as JAK1, JAK2, JAK3 or TYK2 protein tyrosine kinases.

In one or more embodiment the invention provides a compound according to general formula (I) for use in the treatment of a disease, which disease is responsive to the inhibition JAK1 kinase activity.

Besides being useful for human treatment, the compounds of the present invention may also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition. The invention therefore relates to a pharmaceutical composition comprising a compound of formula (I), optionally together with one or more other therapeutically active compound(s), together with a pharmaceutically acceptable excipient, vehicle or carrier(s). The excipient must be "acceptable" in the sense of being compatible with the other ingredients of the composition and not deleterious to the recipient thereof.

Conveniently, the active ingredient comprises from 0.0001-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.001 mg and 1000 mg, preferably between 0.1 mg and 300 mg, more preferred 1-150 mg, such as 3-100 mg of a compound of formula (I).

A suitable dosage of the compound of the invention will depend, inter alia, on the age and condition of the patient, the severity of the disease to be treated and other factors well known to the practising physician. The compound may be administered either orally, parenterally, topically, transdermally or interdermally and other routes according to different dosing schedules, e.g. daily, weekly or with monthly intervals. In general a single dose will be in the range from 0.001 to 400 mg/kg body weight, such as 0.1 g-4 mg/kg. The compound may be administered as a bolus (i.e. the entire daily dosis is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid, semisolid or liquid pharmaceutical diluents or carriers.

The term "usage unit" in connection with topical use means a unitary, i.e. a single dose, capable of being administered topically to a patient in an application per square centimetre of the treatment area of from 0.001 microgram to 1 mg and preferably from 0.05 microgram to 0.5 mg of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult *Goodman & Gilman's The Pharmacological Basis of Therapeutics*, $9^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral, rectal, parenteral (including subcutaneous, intraperitoneal, intramuscular, intraarticular and intravenous), transdermal, intradermal, ophthalmic, topical, nasal, sublingual or buccal administration.

The formulations may conveniently be presented in dosage unit form and may be prepared by but not restricted to any of the methods well known in the art of pharmacy, e.g. as disclosed in Remington, The Science and Practice of Pharmacy, 21ed ed., 2005. All methods include the step of bringing the active ingredient into association with the carrier, which constitutes one or more accessory ingredients. In general, the formulations are prepared by uniformly and intimately bringing the active ingredient into association with a liquid carrier, semisolid carrier or a finely divided solid carrier or combinations of these, and then, if necessary, shaping the product into the desired formulation.

Formulations of the present invention suitable for oral and buccal administration may be in the form of discrete units as capsules, sachets, tablets, chewing gum or lozenges, each containing a predetermined amount of the active ingredient; in the form of a powder, granules or pellets; in the form of a solution or a suspension in an aqueous liquid or non-aqueous liquid; or in the form of a gel, a nano- or micro-emulsion, an oil-in-water emulsion, a water-in-oil emulsion or other dispensing systems. Suitable dispersing or suspending agents for aqueous suspensions include synthetic or natural surfactants and viscosifying agents. The active ingredients may also be administered in the form of a bolus, electuary or paste.

A tablet may be made by compressing, moulding or freeze drying the active ingredient optionally with one or more accessory ingredients. Compressed tablets may be prepared by compressing, in a suitable machine, the active ingredient(s) in a free-flowing form such as a powder or granules, optionally mixed by a binder and/or filler; a lubricant; a disintegrating agent such or a dispersing agent. Moulded tablets may be made by moulding, in a suitable machine, a mixture of the powdered active ingredient and suitable carrier moistened with an inert liquid diluent. Freeze dried tablets may be formed in a freeze-dryer from a solution of the drug substance. A suitable filler can be included.

Formulations for rectal administration may be in the form of suppositories in which the compound of the present invention is admixed with low melting point, water soluble or insoluble solids.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution.

Furthermore, the formulation may contain co-solvent, solubilising agent and/or complexation agents. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula (I) may be presented as a sterile, solid preparation, e.g. a freeze-dried powder, which is readily dissolved in a sterile solvent immediately prior to use.

Transdermal formulations may be in the form of a plaster, patch, microneedles, liposomal or nanoparticulate delivery systems or other cutaneous formulations applied to the skin.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical, such as dermal, intradermal or ophthalmic administration include liquid or semi-solid preparations such as liniments, lotions, gels, applicants, sprays, foams, film-forming systems, microneedles, micro- or nano-emulsions, oil-in-water or water-in-oil emulsions such as creams, ointments or pastes; or solutions or suspensions such as drops.

For topical administration, the compound of formula (I) may typically be present in an amount of from 0.001 to 20% by weight of the composition, such as 0.01% to about 10%, but may also be present in an amount of up to about 100% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula (I) may include one or more additional ingredients such as diluents, buffers, flavouring agents, colourant, surface active agents, thickeners, penetration enhancing agents, solubility enhancing agents preservatives, e.g. methyl hydroxybenzoate (including anti-oxidants), emulsifying agents and the like.

Methods of Preparation

The compounds of the present invention can be prepared in a number of ways well known to those skilled in the art of synthesis. The compounds of formula (I) may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used. The compounds of the present invention or any intermediate may be purified if required using standard methods well known to a synthetic organist chemist, e.g. methods described in "Purification of Laboratory Chemicals", $6^{th}$ ed. 2009, W. Amarego and C. Chai, Butterworth-Heinemann. Starting materials are either known compounds, commercially available, or they may be prepared by routine synthetic methods well known to a person skilled in the art.

General Procedures, Preparations and Examples

Starting materials were commercially available or known in the literature. Reagents and solvents were commercially available and were used without purification unless otherwise noted. Chromatographic purification was performed using a Grace REVELERIS® system with pre-packed REVELERIS® Silica Flash Cartridges, or a Teledyne Isco CombiFlash® Rf system, or manually using silica gel 60. $^1$H NMR spectra were recorded on Bruker instruments at 300, 400, or 600 MHz with tetramethylsilane (6=0.00 ppm) as internal standard. Chemical shift values (6, in ppm) are quoted relative to internal tetramethylsilane (6=0.00) standards. The value of a multiplet, either defined doublet (d), triplet (t), quartet (q) or not (m) at the approximate midpoint is given unless a range is quoted. (br) indicates a broad peak, whilst (s) indicates a singlet.

The following abbreviations have been used throughout:

AcOH acetic acid
Boc tert-butoxycarbonyl
Cbz benzyloxycarbonyl
DCM dichloromethane
dba dibenzylideneacetone
DIPEA N,N-diisopropylethylamine
DMF N,N-dimethylformamide
DMP Dess-Martin periodinane
DMSO dimethyl sulfoxide
DSC Differential scanning calorimetry
ee enantiomeric excess
Et ethyl
EtOAc ethyl acetate
EtOH ethanol
h hours(s)
HATU 1-[bis(dimethylamino)methylene]-1H-1,2,3-triazolo[4,5-b]pyridinium 3-oxide hexafluorophosphate
HPLC high-performance liquid chromatography
HRMS high resolution mass spectrum
L litre
m milli
MeCN acetonitrile
MeOH methanol
min minute(s)
m.p. melting point
Ms methane sulfonyl
MS mass spectrometry or mass spectrum
NMR nuclear magnetic resonance spectroscopy
rt room temperature, i.e. 18-30° C. and typically 20° C.
RuPhos 2-dicyclohexylphosphino-2',6'-diisopropoxybiphenyl
SFC supercritical fluid chromatography
TBS tert-butyldimethylsilyl
TFA trifluoroacetic acid
THF tetrahydrofuran
Tj temperature of heat jacket
TLC thin layer chromatography
tr retention time
Tr temperature of reaction mixture
UHPLC ultra high performance liquid chromatography
UPLC ultra high performance liquid chromatography
Xantphos 4,5-bis(diphenylphosphino)-9,9-dimethylxanthene Preparative HPLC Acidic Method Apparatus: Gilson HPLC system with Gilson UV/VIS-155 detector Column: Waters SunFire™ Prep C18 5 μm OBD 19×250 mm Reagents: (A) 0.1% formic acid-water solution; (B) MeCN Pump:

flow: 30 mL/min

| Time [min] | [%] B |
|---|---|
| 0.0 | 10 |
| 2.0 | 10 |
| 9.0 | 100 |
| 13.0 | 100 |

Basic Method

Apparatus: Gilson HPLC system with Gilson UV/VIS-155 detector

Column: Waters XBridge® Prep C18 5 μm OBD 19×250 mm

Reagents: (A) 50 mM $NH_4HCO_3$ solution; (B) MeCN

Pump:

flow: 30 mL/min

| Time [min] | [%] B |
|---|---|
| 0.0 | 0 |
| 2.0 | 0 |
| 9.0 | 60 |

-continued

| Time [min] | [%] B |
|---|---|
| 10.0 | 100 |
| 13.0 | 100 |

Analytical LC-MS

Method A

Apparatus: Shimadzu UHPLC 2020

Column: Acquity UPLC HSS C18, 1.8 μm, 2.1×50 mm

Reagents:—Formic acid ≥98%, Sigma-Aldrich

Acetonitrile for HPLC UV/gradient grade, Baker

Dimethyl sulfoxide pure (DMSO), Chempur purified water for HPLC

HPLC conditions:—Wavelength: 214 nm±4 nm, 254 nm±4 nm

Flow: 0.5 ml/min

Column temperature: 25° C.

Autosampler temperature: 20° C.

Injection volume: 3.0 μl

Analysis time: 6 min

Elution: gradient

| Time [min] | Mobile phase A [%] | Mobile phase B [%] | Flow [ml/min] |
|---|---|---|---|
| 0.0 | 95 | 5 | 0.5 |
| 4.0 | 5 | 95 | 0.5 |
| 5.0 | 5 | 95 | 0.5 |
| 5.2 | 95 | 5 | 0.5 |
| 6.0 | 95 | 5 | 0.5 |

Mobile phase A: 0.1% v/v water solution of formic acid

Mobile phase B: 0.1% v/v acetonitrile solution of formic acid

Solution for syringe washing: 20% MeOH

Ms Conditions:

Mass range: 100-1000 m/z

Ionization: alternate

Scan time: 0.5 s

Method B

UPLC-MS analyses were performed using a Waters Acquity UPLC system with a 2.1×50 mm Acquity UPLC® HSS T3 1.8 μm column and an Acquity SQ Detector operated in positive ionization electrospray mode. The mobile phases consisted of 0.1% formic acid in an aqueous 10 mM ammonium acetate solution for buffer A and 0.1% formic acid in acetonitrile for buffer B. A binary gradient (A:B 95:5-5:95) over 1.4 min was used with a flow rate of 1.2 mL/min and the column temperature was 60° C.

Method C

UPLC-MS analyses with high resolution mass spectra were performed using a Waters Acquity UPLC system with UV detection at 254 nm and a Waters LCT Premier XE high resolution TOF mass spectrometer operated in positive ionization electrospray mode. The same column and mobile phases A and B as in method B were used, but with a slower gradient (A:B 99:1-1:99 over 4.8 min; 0.7 mL/min; column temp. 40° C.).

Method D

LC-MS: The mass spectra were obtained on a Shimadzu LCMS-2010EV spectrometer using electrospray ionization and atmospheric-pressure chemical ionization; Column: Acquity BEH C18 (50 mm×2.1 mm, 1.7 Lm); Mobile Phase: A: 0.1% Formic Acid in water; B: 0.1% Formic Acid in acetonitrile; Gradient: Time (min)/% B: 0/2, 0.2/2, 2.3/98, 3.4/98, 3.41/2, 3.5/2; Column Flow Rate: 0.8 mL/min.

Method E

LC-MS: The mass spectra were obtained on a Shimadzu LCMS-2010EV spectrometer using electrospray ionization and atmospheric-pressure chemical ionization; Column: Acquity BEH C18 (50 mm×2.1 mm, 1.7 μm); Mobile Phase: A: 0.1% Formic Acid in water; B: 0.1% Formic Acid in acetonitrile; Gradient time (min)/% B: 0/3, 0.4/3, 2.5/98, 3.4/98, 3.5/3, 4/3; Column Temp: 35° C., Flow Rate: 0.6 mL/min.

Analytical Chiral Stationary Phase SFC

Chiral stationary phase SFC analyses were performed using a Waters UPC2 SFC instrument with a Phenomenex Lux® 3 μm Cellulose-4 (150×4.6 mm) column. Isocratic conditions with a mobile phase consisting of $CO_2$:MeOH 80:20 and a flow rate of 3 mL/min were used. Enantiomeric ratios of analytes were determined by integration of UV peak areas.

Intermediates

Intermediate 1

2-[trans-4-[(2-Chloro-5-nitropyridin-4-yl)amino]cyclohexyl]acetonitrile

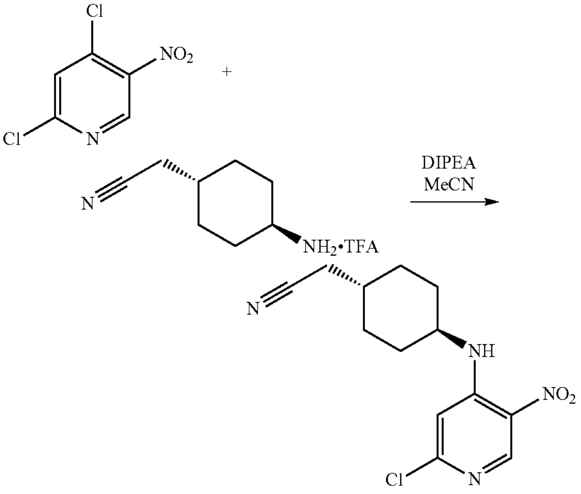

A solution of trans-4-(cyanomethyl)cyclohexyl]ammonium trifluoroacetate (Li, Y.-L. et al. US2014/0121198) (26.7 g, 105.8 mmol) and 2,4-dichloro-5-nitropyridine (22.4 g, 116.3 mmol) in dry acetonitrile was chilled in an ice bath and N,N-diisopropylethylamine (55.3 mL, 317 mmol) was added dropwise. The resulting mixture was stirred at rt for 20 h. The reaction mixture was diluted with saturated aqueous $NaHCO_3$ and extracted with DCM (3×500 mL). The combined organic layers were dried over $Na_2SO_4$, filtered and evaporated under vacuum. The crude product was triturated with hexane, diethyl ether and water to afford the title compound (29.8 g, 95%) as a yellow solid.

UPLC-MS (Method A): $t_R$=3.41 min, m/z=294.9 (M+H$^+$).

$^1$H NMR (400 MHz, DMSO-$d_6$) δ 8.87 (s, 1H), 8.03 (d, J=8.3 Hz, 1H), 7.30 (s, 1H), 3.73 (dtd, J=11.5, 7.7, 4.2 Hz, 1H), 2.50 (d, J=4.2 Hz, 2H) 2.04-1.91 (m, 2H), 1.86-1.75 (m, 2H), 1.64 (ddd, J=11.6, 5.7, 3.0 Hz, 1H), 1.53-1.39 (m, 2H), 1.31 (ddd, J=25.4, 12.9, 4.2 Hz, 2H).

Intermediate 2

2-[trans-4-[(5-Amino-2-chloropyridin-4-yl)amino]cyclohexyl]acetonitrile

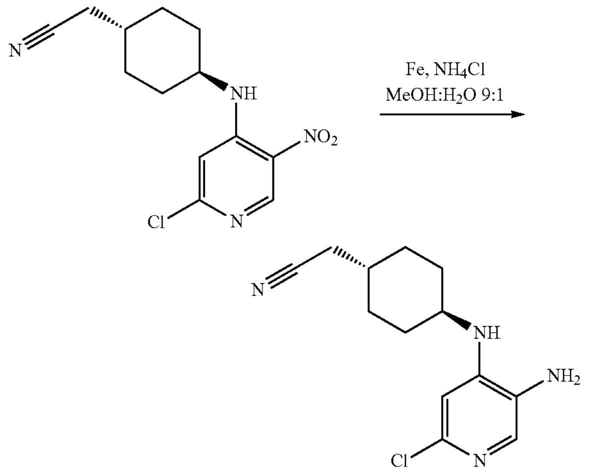

To a solution of Intermediate 1 (3.5 g, 11.9 mmol) in MeOH:water 9:1 (99 mL) were added iron (1.86 g, 33.2 mmol) and ammonium chloride (1.91 g, 35.6 mmol). The resulting mixture was stirred at reflux for 5 h. After cooling to rt, the solids were removed by filtration through a celite plug. The cake was washed with MeOH and the filtrate was concentrated to remove the volatiles. The residue was diluted with saturated aq. $NaHCO_3$ (50 mL) and extracted with EtOAc (3×30 mL). The organic phase was dried over $Na_2SO_4$ and concentrated in vacuo giving the title compound as a brown solid (3.0 g, 95%).

UPLC-MS (Method A): $t_R$=1.85 min, m/z=265 ($M+H^+$).

$^1$H NMR (400 MHz, DMSO-$d_6$) δ 7.37 (s, 1H), 6.37 (s, 1H), 5.38 (d, J=7.7 Hz, 1H), 4.74 (s, 2H), 2.48 (d, J=6.4 Hz, 2H), 2.06-1.92 (m, 2H), 1.87-1.74 (m, 2H), 1.71-1.57 (m, 1H), 1.33-1.16 (m, 5H).

Intermediate 3

2-[trans-4-[6-Chloro-2-(1-hydroxyethyl)-1H-imidazo[4,5-c]pyridin-1-yl]cyclohexyl]-acetonitrile

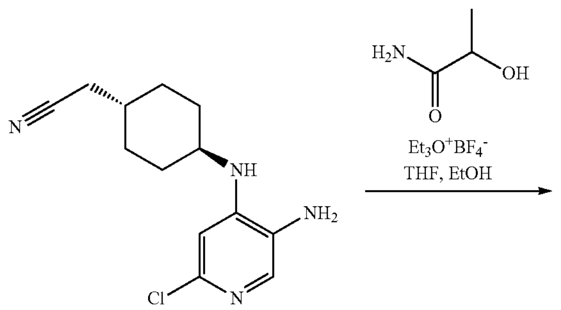

-continued

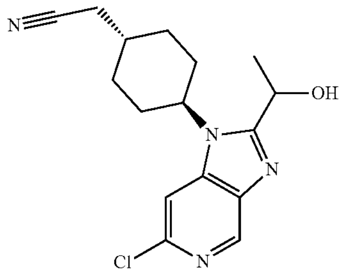

A mixture of triethyloxonium tetrafluoroborate (9.3 g, 49.1 mmol) and lactamide (4.4 g, 49.1 mmol) in THF (40 mL) was stirred at rt for 2 h (clear solution). This solution was added to a solution of Intermediate 2 (2.6 g, 9.8 mmol) in EtOH (70 mL). The obtained mixture was heated to reflux for 18 h. The reaction mixture was concentrated and the residue was partitioned between water (40 mL) and EtOAc (25 mL). The aqueous phase was extracted with EtOAc (3×20 mL). The organic phase was dried over $Na_2SO_4$ and concentrated in vacuo. Column chromatography (20% of EtOAc in DCM and 10% of MeOH in DCM as eluent) afforded a semisolid that was triturated with diethyl ether giving the title compound as a reddish solid (2.3 g, 73%).

UPLC-MS (Method A): $t_R$=2.52 min, m/z=319 ($M+H^+$).

$^1$H NMR (400 MHz, DMSO-$d_6$) δ 8.70 (s, 1H), 8.02 (s, 1H), 5.81 (d, J=6.8 Hz, 1H), 5.10 (p, J=6.5 Hz, 1H), 4.74-4.60 (m, 1H), 2.55 (d, J=6.1 Hz, 2H), 2.39-2.17 (m, 2H), 2.16-2.03 (m, 1H), 1.98-1.84 (m, 4H), 1.60 (d, J=6.5 Hz, 3H), 1.38-1.22 (m, 2H).

EXAMPLES

Example 1 trans-2-[4-[2-[1-Hydroxyethyl]-6-(methylamino)imidazo[4,5-c]pyridin-1-yl]cyclohexyl]acetonitrile (Compound 1)

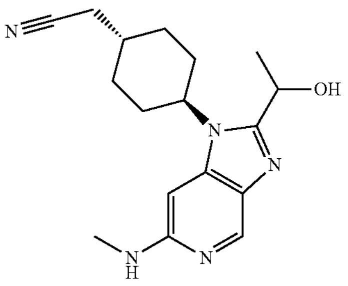 [SMILES: CNc1cc2c(cn1)nc(C(C)O)n2[C@H]1CC[C@H](CC#N)CC1]

Step 1

2-[trans-4-[6-Amino-2-(1-hydroxyethyl)-1H-imidazo[4,5-c]pyridin-1-yl]cyclohexyl]-acetonitrile

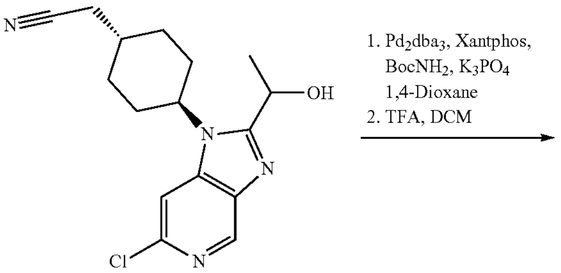

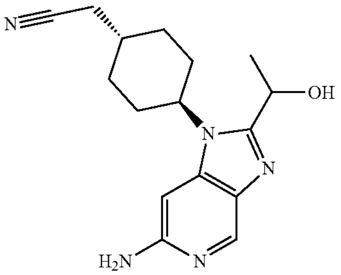

Intermediate 3 (0.20 g, 0.63 mmol), tert-butyl carbamate (0.15 g, 1.25 mmol), tris-(dibenzylideneacetone)dipalladium(0) (0.06 g, 0.06 mmol), 4,5-bis(diphenylphosphino)-9,9-dimethylxanthene (0.11 g, 0.19 mmol) and tribasic potassium phosphate (0.31 g, 1.44 mmol) were mixed in 1,4-dioxane (15 mL). The obtained mixture was degassed with argon for 20 min and then heated at 130° C. under microwave irradiation for 45 min. The mixture was filtered through a celite plug, the cake was washed with MeOH/DCM (1:9) and the filtrate was concentrated. This reaction was repeated additionally four times using the same amounts and conditions due to the volume limitations of the microwave reactor. The residues obtained were combined. Short column chromatography (2% of MeOH in DCM as eluent) afforded a crude mixture (0.7 g) that was dissolved in DCM (15 mL). To the solution was added dropwise TFA (1.3 mL, 17.5 mmol). The obtained mixture was stirred at rt for 24 h. The mixture was concentrated in vacuo. The residue was dissolved in DCM (15 mL) and washed with aq. $NaHCO_3$ (5 mL). The aqueous phase was extracted with DCM (5×15 mL). The organic phase was dried over $Na_2SO_4$ and concentrated in vacuo. Column chromatography (gradient from MeOH:DCM 4:96 to 7.5M $NH_3$ in MeOH:DCM 5:95) afforded the title compound as a yellowish foam (0.195 g, 21%).

UPLC-MS (Method A): $t_R$=1.72 min, m/z=300 (M+$H^+$).

$^1$H NMR (400 MHz, DMSO-$d_6$) δ 8.26 (d, J=0.9 Hz, 1H), 6.66 (d, J=1.0 Hz, 1H), 5.59 (d, J=6.7 Hz, 1H), 5.39 (s, 2H), 4.96 (p, J=6.6 Hz, 1H), 4.62-4.47 (m, 1H), 2.57 (d, J=6.4 Hz, 2H), 2.23-2.06 (m, 2H), 2.01-1.72 (m, 5H), 1.54 (d, J=6.5 Hz, 3H), 1.40-1.22 (m, 2H).

Step 2 trans-2-[4-[2-[1-Hydroxyethyl]-6-(methylamino)imidazo[4,5-c]pyridin-1-yl]cyclohexyl]acetonitrile

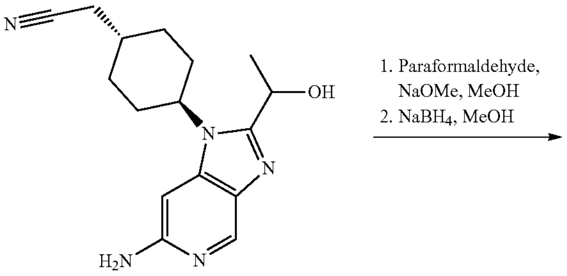

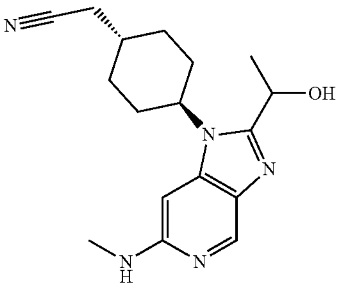

To a solution the product of Step 1 (0.195 g, 0.65 mmol) in methanol (5 mL) was added paraformaldehyde (0.078 g, 2.61 mmol) and sodium methoxide (0.176 g, 3.26 mmol). The obtained mixture was heated to reflux. After 2 h, the mixture was cooled to 0° C. and sodium borohydride (0.099 g, 2.61 mmol) was added. The resulting mixture was heated at reflux for 1 h. After cooling to rt, the reaction was quenched by carefully addition of saturated aq. $NaHCO_3$ (10 mL). The aqueous phase was extracted with EtOAc (3×10 mL). The organic phase was dried over $Na_2SO_4$ and concentrated in vacuo. Column chromatography (4% to 10% MeOH in DCM as eluent) afforded the title compound as a white foam (0.152 g, 76%).

HPLC-MS (Method C): $t_R$=1.67 min, m/z=314.1939 (M+H*).

$^1$H NMR (400 MHz, DMSO-$d_6$) δ 8.34 (d, J=0.9 Hz, 1H), 6.48 (d, J=0.9 Hz, 1H), 5.90 (q, J=4.9 Hz, 1H), 5.59 (d, J=6.6 Hz, 1H), 4.96 (p, J=6.6 Hz, 1H), 4.61-4.50 (m, 1H), 2.80 (d, J=4.9 Hz, 3H), 2.56 (d, J=6.2 Hz, 2H), 2.30-2.11 (m, 2H), 1.98-1.82 (m, 5H), 1.55 (d, J=6.5 Hz, 3H), 1.39-1.23 (m, 2H).

Examples 2 and 3 trans-2-[4-[2-[(1S)-1-Hydroxyethyl]-6-(methyl-amino)imidazo[4,5-c]pyridin-1-yl]cyclo-hexyl]acetonitrile (Compound 2) and trans-2-[4-[2-[(1R)-1-Hydroxyethyl]-6-(methyl-amino)imidazo[4,5-c]pyridin-1-yl]cyclohexyl]acetonitrile (Compound 3)

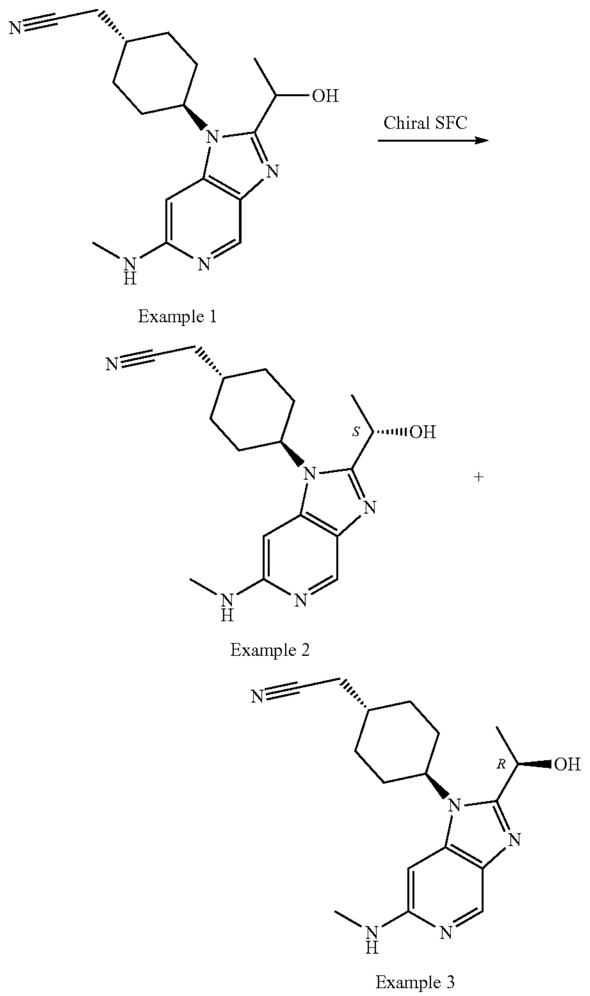

The enantiomers of Example 1 (166 mg) were separated by chiral stationary phase SFC using the following conditions:

| | |
|---|---|
| Column | Amy-C (20 × 250 mm, 5 μm) |
| Column temperature | 40° C. |
| Flow rate | 50 mL/min |
| Back-pressure regulator | 125 bar |
| Detector wavelength | 228 nm |
| Injection volume/sample mass | 300 μL/12 mg |
| Eluent (isochratic) | 30:70 MeOH:$CO_2$ + 0.1% v/v $NH_3$ |

The absolute configurations were established by comparison with a sample of the (R) enantiomer prepared from (R)-lactamide, see Example 3 (alternative preparations) below.

Example 2 (Compound 2)

Yield: 73 mg, >98% ee

UPLC-MS (Method C): $t_R$=1.67 min, m/z=314.1908 ($M+H^+$).

$^1$H NMR (300 MHz, DMSO-$d_6$) δ 8.33 (d, J=0.8 Hz, 1H), 6.47 (d, J=1.0 Hz, 1H), 5.89 (q, J=5.0 Hz, 1H), 5.58 (d, J=6.7 Hz, 1H), 4.96 (p, J=6.5 Hz, 1H), 4.63-4.47 (m, 1H), 2.79 (d, J=5.0 Hz, 3H), 2.55 (d, J=6.1 Hz, 2H), 2.30-2.10 (m, 2H), 2.01-1.76 (m, 5H), 1.54 (d, J=6.4 Hz, 3H), 1.40-1.20 (m, 2H).

Example 3 (Compound 3)

Yield: 67 mg, >98% ee

UPLC-MS (Method C): $t_R$=1.67 min, m/z=314.1975 ($M+H^+$).

$^1$H NMR (300 MHz, DMSO-$d_6$) δ 8.33 (d, J=0.9 Hz, 1H), 6.47 (d, J=1.1 Hz, 1H), 5.89 (q, J=4.9 Hz, 1H), 5.58 (d, J=6.5 Hz, 1H), 4.96 (p, J=6.4 Hz, 1H), 4.63-4.46 (m, 1H), 2.79 (d, J=5.0 Hz, 3H), 2.55 (d, J=6.1 Hz, 2H), 2.29-2.11 (m, 2H), 2.00-1.77 (m, 5H), 1.54 (d, J=6.5 Hz, 3H), 1.39-1.19 (m, 2H).

$^1$H NMR (600 MHz, DMSO-$d_6$) 8.33 (d, J=0.9 Hz, 1H), 6.48 (d, J=1.0 Hz, 1H), 5.90 (q, J=5.0 Hz, 1H), 5.59 (d, J=6.7 Hz, 1H), 4.96 (p, J=6.6 Hz, 1H), 4.55 (tt, J=12.3, 4.0 Hz 1H), 2.79 (d, J=5.0 Hz, 3H), 2.55 (d, J=6.4 Hz, 2H), 2.20 (qdd, J=12.8, 10.4, 3.7 Hz, 2H), 1.93 (ddd, J=13.1, 6.3, 3.2 Hz, 2H), 1.89-1.86 (m, 2H), 1.86-1.84 (m, 1H), 1.54 (d, J=6.5 Hz, 3H), 1.30 (qdt, J=12.3, 7.6, 3.6 Hz, 2H). $^{13}$C NMR (151 MHz, DMSO-$d_6$) δ 155.5, 155.4, 141.3, 139.2, 133.3, 119.5, 86.4, 61.9, 54.0, 32.9, 30.7, 30.7, 29.1, 28.8, 28.8, 22.9, 21.5.

Example 3 (Alternative Preparation No. 1)

trans-2-[4-[2-[(1R)-1-Hydroxyethyl]-6-(methyl-amino)imidazo[4,5-c]pyridin-1-yl]cyclo-hexyl]acetonitrile (Compound 3)

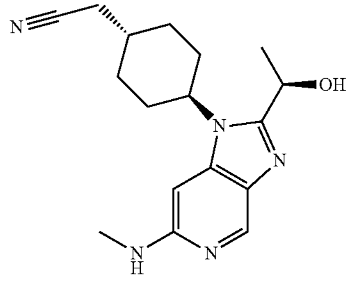 [SMILES: CNc1cc2c(cn1)nc([C@@H](C)O)n2[C@H]1CC[C@H](CC#N)CC1]

Step 1

2-[trans-4-[6-Chloro-2-[(1R)-1-hydroxyethyl]-1H-imidazo[4,5-c]pyridin-1-yl]cyclo-hexyl]acetonitrile

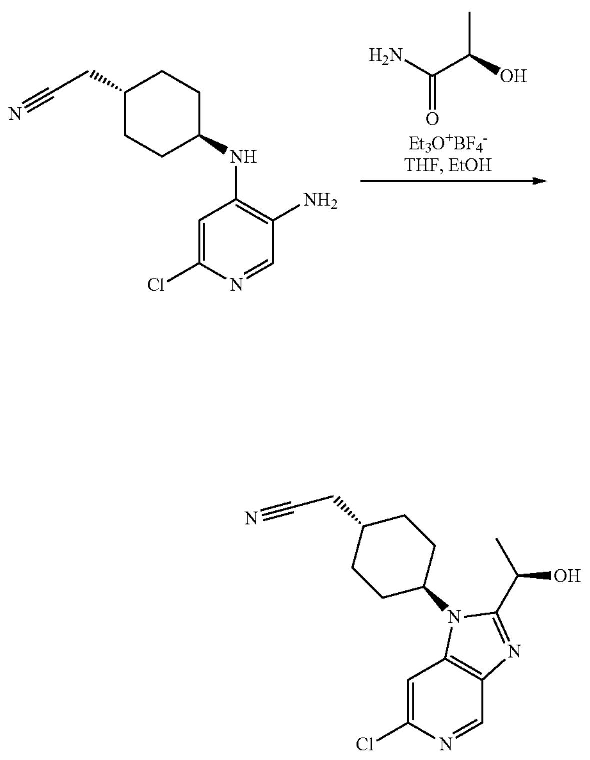

A 100 mL screwcap vial was charged with triethyloxonium tetrafluoroborate (8.00 g, 42.1 mmol) and dry THF (30 mL) under argon. To the white suspension was added (R)-lactamide (3.87 g, 42.1 mmol) in one portion. The resulting solution was stirred at rt. After ~6 min, a weakly exothermic reaction occurred and the reaction vessel was cooled in a water bath. After 2 h at rt, this solution was added to a suspension of Intermediate 2 (2.23 g, 8.42 mmol) in anhydrous ethanol (45 mL) and the resulting solution was stirred at 80° C. overnight. Volatiles were evaporated and the residue was treated with sat. aq. sodium bicarbonate solution (50 mL). The mixture was extracted with EtOAc (3×80 mL) and the combined organic phases were washed with brine (50 mL), dried over sodium sulfate and filtered. Evaporation of volatiles afforded a residue (13.5 g) that was purified using flash chromatography (DCM:MeOH 98:2 to 95:5) to afford a brown foam (1.92 g). This was triturated with ether (20 mL) to afford the title compound as a solid (1.62 g, 57%).

UPLC-MS (Method B): $t_R$=0.52 min, m/z=319.2 ($M+H^+$).

$^1H$ NMR (300 MHz, DMSO-$d_6$) δ 8.69 (d, J=0.8 Hz, 1H), 8.00 (d, J=0.9 Hz, 1H), 5.80 (d, J=6.8 Hz, 1H), 5.10 (p, J=6.5 Hz, 1H), 4.74-4.59 (m, 1H), 2.54 (d, J=6.4 Hz, 2H), 2.38-2.16 (m, 2H), 2.17-2.00 (m, 1H), 1.99-1.81 (m, 4H), 1.59 (d, J=6.5 Hz, 3H), 1.41-1.18 (m, 2H).

The absolute configuration of the title compound was confirmed by single crystal X-ray diffraction.

Step 2

2-[4-[2-[(1R)-1-[tert-Butyl(dimethyl)silyl]oxyethyl]-6-chloro-imidazo[4,5-c]pyridin-1-yl]cyclohexyl] acetonitrile

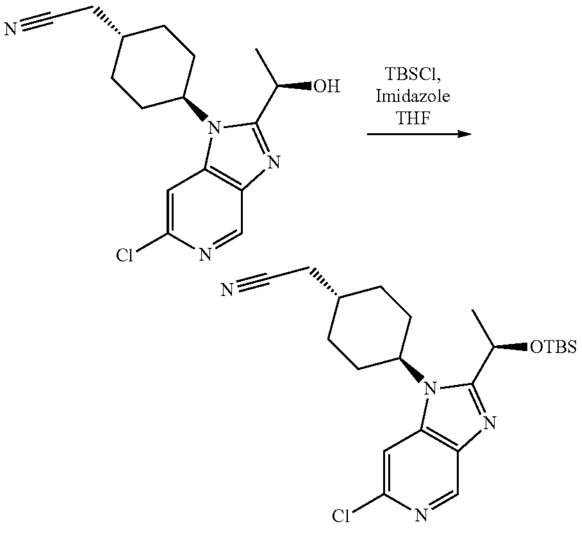

A solution of the product of Step 1 (2.47 g, 7.75 mmol) in THF (35 mL) was cooled in an ice bath and imidazole (791 mg, 11.6 mmol) was added. After 5 min, a solution of TBSCl (1.28 g, 8.52 mmol) in THF (11 mL) was added and the ice bath was removed. After 5 h at rt the mixture was warmed to 45° C. and stirred at this temperature overnight. To effect complete conversion, another portion of imidazole (791 mg, 11.6 mmol) and a solution of TBSCl (1.28 g, 8.52 mmol) in THF (5 mL) were added. The mixture was stirred to 45° C. for another 24 h and was poured into a mixture of brine (35 mL) and water (35 mL). It was extracted with EtOAc (2×80 mL), the organic layers were washed with brine, dried over $Na_2SO_4$, filtered, and evaporated. The residue was purified by flash chromatography (DCM:EtOAc 90:10 to 80:20) to afford the title compound (2.95 g, 83%) as a solid.

UPLC-MS (Method B): $t_R$=0.92 min, m/z=433.3 ($M+H^+$).

$^1H$ NMR (600 MHz, $CDCl_3$) δ 8.75 (d, J=0.8 Hz, 1H), 7.42 (d, J=0.9 Hz, 1H), 5.34 (q, J=6.8 Hz, 1H), 5.00 (tt, J=12.5, 4.1 Hz, 1H), 2.41 (d, J=6.4 Hz, 2H), 2.31-2.19 (m, 2H), 2.17-2.09 (m, 2H), 2.09-2.03 (m, 2H), 2.00-1.91 (m, 1H), 1.62 (d, J=6.4 Hz, 3H), 1.48-1.33 (m, 2H), 0.91 (s, 9H), 0.14 (s, 3H), 0.03 (s, 3H).

Step 3

2-[4-[2-[(1R)-1-[tert-Butyl(dimethyl)silyl]oxyethyl]-6-[(4-methoxyphenyl)methyl-methyl-amino]imidazo [4,5-c]pyridin-1-yl]cyclohexyl]acetonitrile

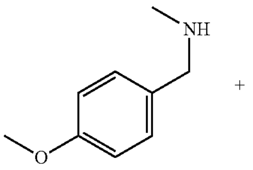

-continued

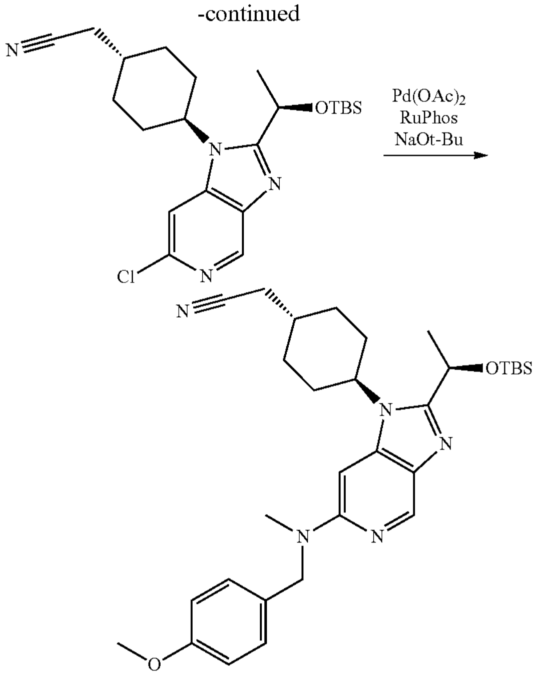

A 2 mL screwcap vial was charged with the product of Step 2 (46.2 mg, 0.107 mmol) and 4-methoxy-N-methylbenzylamine (32.3 mg, 0.213 mmol). The vial was flushed with argon, and a mixture of sodium tert-butoxide (12.3 mg, 0.128 mmol), RuPhos (3.0 mg, 0.0064 mmol) and palladium (II) acetate (0.72 mg, 0.0032 mmol) was added. The mixture was stirred under argon for 17 h at 110° C. It was cooled to rt and dichloromethane (0.45 mL) was added. The mixture was washed with brine:water 2:1 (0.45 mL) and the aqueous layer was extracted with dichloromethane (2×0.45 mL). The combined organic layers were dried over $Na_2SO_4$, filtered and evaporated to afford a crude product containing the title compound and the corresponding des-TBS analogue (75.3 mg). This material was used in the next step without purification.

UPLC-MS (Method B): $t_R$=0.95 min, m/z=548.4 (M+H$^+$).

Step 4 trans-2-[4-[2-[(1R)-1-Hydroxyethyl]-6-(methylamino)imidazo[4,5-c]pyridin-1-yl]cyclo-hexyl]acetonitrile

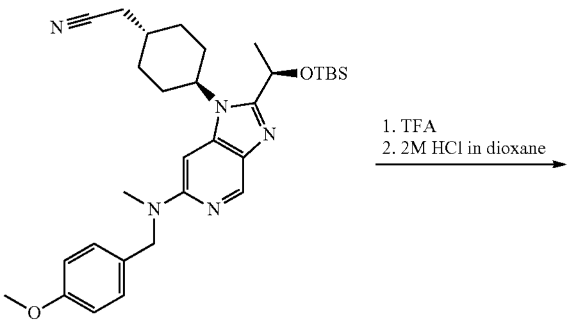

-continued

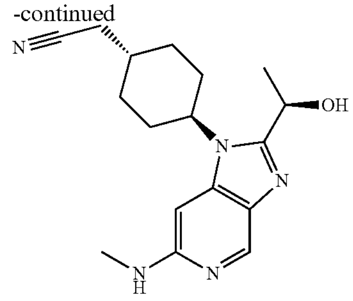

The crude product from Step 3 was dissolved in TFA (0.25 mL) at 0° C. and the mixture was stirred at rt for 1.5 h. Volatiles were removed under vacuum and the residue was dissolved in 4 M hydrogen chloride in dioxane (0.25 mL). The mixture was stirred at rt for 18 h, volatiles were evaporated, and the residue was dissolved in dichloromethane (0.25 mL). To this was added 2 M ammonia in methanol (0.60 mL) to adjust pH to ~10. Volatiles were removed under vacuum, the residue was dissolved in DCM:MeOH 95:5 (2 mL) and the mixture was filtered. The filtrate was evaporated and the residue was purified by chromatography (4 g pre-packed silica gel column eluted with DCM:MeOH 96:4 to 94:6) to afford the title compound (37.7 mg) as a semi-solid containing ca. 30% of 4-methoxy-N-methylbenzylamine.

UPLC-MS (Method B): $t_R$=0.38 min, m/z=314.3 (M+H$^+$).

Analytical chiral stationary phase SFC: (S) enantiomer (minor) $t_R$=5.37 min; (R) enantiomer (major) $t_R$=5.78 min.

Example 3 (Alternative Preparation No. 2)

trans-2-[4-[2-[(1R)-1-Hydroxyethyl]-6-(methylamino)imidazo[4,5-c]pyridin-1-yl]cyclohexyl]acetonitrile (Compound 3)

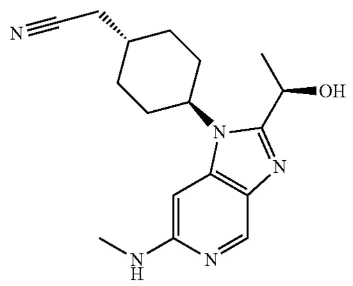 [SMILES: CNc1cc2c(cn1)nc([C@@H](C)O)n2[C@H]1CC[C@H](CC#N)CC1]

Step 1

2-[trans-4-[(2-Chloro-5-nitropyridin-4-yl)amino]cyclohexyl]acetonitrile

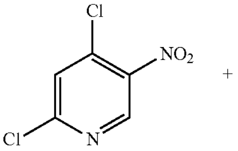

-continued

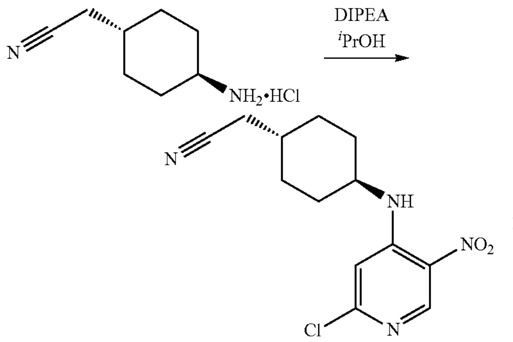

A 20 L glass reactor, equipped with mechanical stirrer, reflux condenser and argon inlet, was evacuated and flushed with argon twice. The reactor was charged with 700 g of 2,4-dichloro-5-nitropyridine (3.63 mol, 1.0 equiv.), 665 g of trans-4-(cyanomethyl)cyclohexyl]ammonium hydrochloride (3.81 mol, 1.05 equiv.) and 7.00 L of 2-propanol. The resulting slurry was stirred at 25° C. and 1.90 L of diisopropylethylamine (1.41 kg, 10.9 mol, 3.0 equiv.) was added. The addition tube was washed with 0.100 L 2-propanol and the slurry was heated towards reflux (Tj setpoint=95° C.). The mixture was stirred at reflux for 15 hours and then cooled to 25° C. In process control (LCMS) showed 99% conversion.

The product was isolated by filtration and washed on the filter with 1.75 L of 2-propanol and then 3.80 L of 2-propanol. The filter cake was transferred to glass bowls and dried in vacuo at 50° C. until constant weight; yielding 1.00 kg (94%) of the title compound as yellow solid; HPLC purity: 98.8 area %.

Step 2

2-[trans-4-[(5-Amino-2-chloropyridin-4-yl)amino] cyclohexyl]acetonitrile

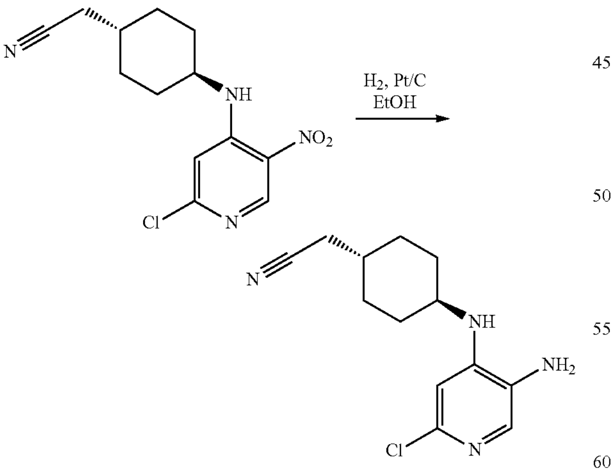

A 2.0 L Parr-shaker reaction flask was flushed with argon and charged with 5.00 g of 5% Pt/C (paste with 50% water, 0.05 g/g, 1.3 mmol), 100 g of 2-[trans-4-[(2-chloro-5-nitropyridin-4-yl)amino]cyclohexyl]acetonitrile (339 mmol) and 1.00 L of ethanol. The Parr-shaker reactor flask was placed in the Parr-shaker and evacuated and refilled with argon twice. Next, the flask was evacuated and refilled with hydrogen. The pressure was adjusted to 1.5 bar and the shaker was started. Additional hydrogen was added several times but after 2 hours the consumption of hydrogen ceased. In process control (HPLC) showed >99% conversion and 600 mL of dichloromethane was added in order to prevent precipitation of the title compound. The resulting mixture was stirred for 10 minutes and filtered over Celite. The filter cake was washed with 250 mL of dichloromethane and the solvents from the combined filtrates were removed by evaporation under reduced pressure at 50° C. The residue was transferred to a glass bowl and dried in vacuo at 50° C. until constant weight, yielding 85.1 g (95%) of the title compound as brown solid; HPLC purity: 94 area %.

Step 3

2-[trans-4-[6-Chloro-2-[(1R)-1-hydroxyethyl]-1H-imidazo[4,5-c]pyridin-1-yl]cyclohexyl]acetonitrile

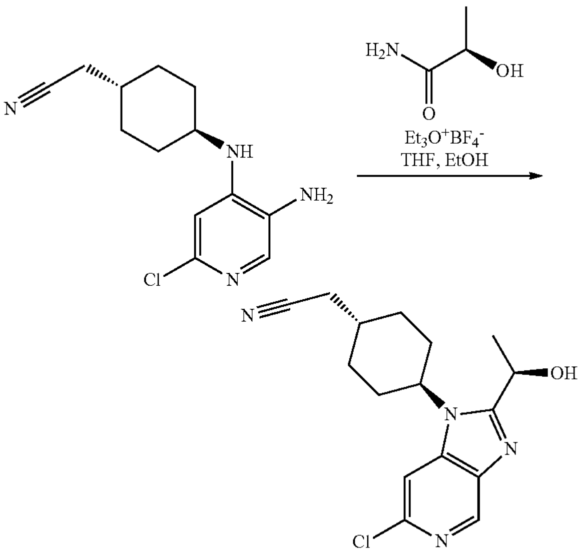

A 20 L glass reactor, equipped with mechanical stirrer, reflux condenser and argon inlet, was evacuated and flushed with argon twice. The reactor was charged with 409 g of (R)-lactamide (4.59 mol, 2.5 equiv.) and 4.90 L of tetrahydrofuran. The temperature was adjusted to 23° C. and 872 g of triethyloxonium tetrafluoroborate (4.59 mol, 2.5 equiv.) was added in one portion. NB! Reaction is exothermal and temperature reached 43° C. after addition. Reaction mixture was cooled and stirred at 23° C. for 90 minutes. The mixture was transferred to 10 L blue cap flask and stored under argon. The reactor was rinsed with 2.7 L of ethanol and the clean reactor was charged with 486 g of 2-[trans-4-[(5-amino-2-chloropyridin-4-yl)amino]cyclohexyl]acetonitrile (1.84 mol, 1.0 equiv.) and 7.3 L of ethanol. The temperature was adjusted to 23° C. and the tetrahydrofuran solution containing (R)-lactamide and triethyloxonium tetrafluoroborate was added over a period of approx. 2-4 minutes. The reaction mixture was heated to reflux (Tr=70° C., Tj setpoint=85° C.). The precipitation of a white salt was observed. The reaction mixture was unclear and orange. After 6 hours, in process control (HPLC) showed >95% conversion and the reaction mixture was cooled to 23° C. and stirred for additionally 16 hours. The mixture was filtered and the filter cake was washed with 2.0 L of tetrahydrofuran. The filtrate was transferred back into the reactor and the solvents were removed by distillation under reduced pressure at 50° C. The distillation was stopped after 7 hours when condensation ceased at Tr=31° C./17 mbar. The residual slurry was diluted with 7.3 L of methyl tert-butylether and 7.3 L of 10% aqueous sodium carbonate. The slurry was stirred at 23° C. for 14 hours after which the title compound was isolated by filtration. The filter cake was washed with 5.0 L of water, sucked dry and transferred back into the reactor. Next, 5.0 L of water were added to the reactor and the resulting slurry was stirred at 23° C. for 60 minutes and filtered. The filter cake was washed with 5.0 L of water and sucked dry. The resulting off white solid was transferred to glass bowls and dried in vacuo at 50° C. until constant weight; typical yield 70-90% of the title compound as off white solid; HPLC purity of wet filter cake 95 area %.

Step 4 trans-2-[4-[2-[(1R)-1-Hydroxyethyl]-6-(methylamino)imidazo[4,5-c]pyridin-1-yl]cyclohexyl]acetonitrile

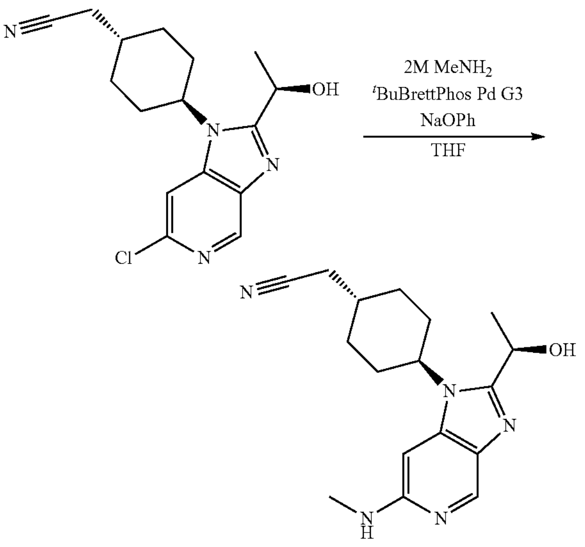

A 400 mL EasyMax glass reactor, equipped with mechanical stirrer, reflux condenser and argon inlet, was flushed with argon. The reactor was charged with 5.43 g of sodium tert-butoxide (56.5 mmol, 1.2 equiv.), 5.54 g of phenol (58.8 mmol, 1.25 equiv.) and 195 mL of tetrahydrofuran. The mixture was stirred at 25° C. for 20 minutes after which 15.0 g of 2-[trans-4-[6-chloro-2-[(1R)-1-hydroxyethyl]-1H-imidazo[4,5-c]pyridin-1-yl]cyclohexyl]acetonitrile (47.1 mmol, 1.0 equiv.) was added. The addition funnel was flushed with 30 mL of tetrahydrofuran and 94.1 mL of 2 M methylamine in tetrahydrofuran (188 mmol, 4.0 equiv.) were added. The resulting mixture was heated towards 55° C. (Tj setpoint=55° C.). In a separate reaction flask, 0.210 g of $^{t}$BuBrettPhos Pd G3 (0.235 mmol, 0.005 equiv.) was dissolved in 4.0 mL of tetrahydrofuran. The $^{t}$BuBrettPhos Pd G3 solution was added to the reaction mixture at 55° C. After 23 hours the dark homogenous solution was cooled to 23° C. and transferred to a separation funnel. The reaction mixture was washed with 2×225 mL of 2 M aqueous sodium hydroxide. The organic phase was concentrated to approx. 50% volume by evaporation under reduced pressure at 50° C. and diluted with 125 mL of heptane.

Silica plug filtration; 105 g of silica gel (7.0 g/g) was activated with 250 mL of heptane/ethyl acetate (1:1) and poured onto a glass filter (8 cm diameter). The organic phase containing crude title compound was slowly loaded onto the silica plug. Impurities were eluted with 2×250 mL of heptane/ethyl acetate (1:1) and then 250 mL of ethyl acetate. Next, the title compound was eluted with 5×200 mL of tetrahydrofuran. The fractions containing the title compound were pooled and the solvent was removed by evaporation under reduced pressure, providing 12.3 g (83%) of crude title compound as brown solid; HPLC purity 95 area %.

Pd scavenging; a 100 mL flask was charged with 3.00 g of the crude title compound (9.57 mmol) and 45 mL of methanol. The mixture was stirred until all solids dissolved and then 0.30 g of SiliaMetS® DMT (10% w/w dimercaptotriazine, 40-63 μm, 60 A) were added. The slurry was heated towards 50° C. and stirred for 4 hours, after which the mixture was cooled to 23° C. and filtered over celite. The filter cake was washed with 6.0 mL of methanol and the solvent was removed from the combined filtrates by evaporation under reduced pressure, yielding 2.75 g (92% recovery) of the title compound.

Re-crystallization; A 100 mL flask was charged 3.00 g (9.57 mmol; HPLC purity 96 area %) of the title compound and 20 mL of ethyl acetate. The mixture was heated towards reflux and stirred until all solids dissolved. The mixture was allowed to cool and then 10 mL of and methyl tert-butylether was added dropwise to the warm solution. The mixture was allowed to cool to room temperature and was stirred for 17 hours. The precipitate was isolated by filtration and washed on the filter with 2×1.0 mL of methyl tert-butylether and dried in vacuo at 50° C. until constant weight, yielding 1.81 g (60%) of the title compound as off white solid (Crystalline, m.p. (DSC onset temperature) 143±2° C.); HPLC purity 98 area %.

Example 4 trans-2-[4-[2-[(1R)-1-Hydroxyethyl]-6-(trideuteriomethylamino)imidazo[4,5-c]pyridin-1-yl]cyclohexyl]acetonitrile (Compound 4)

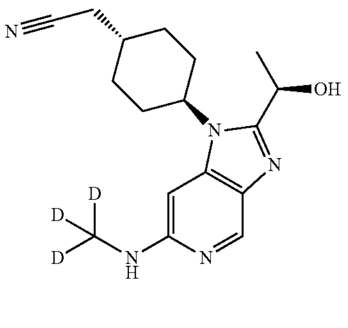

Step 1

1,1,1-Trideuterio-N-[(4-methoxyphenyl)methyl] methanamine

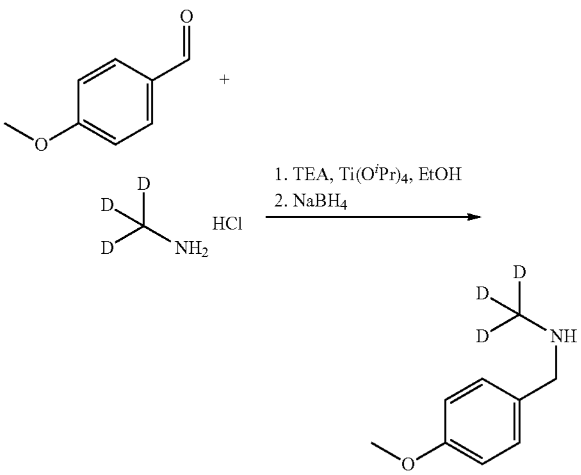

To a mixture of 4-methoxybenzaldehyde (0.243 mL, 2.00 mmol) in anhydrous ethanol (3.0 mL) under argon was at rt added trideuteriomethanamine hydrochloride (282 mg, 4.00 mmol) and TEA (0.558 mL, 4.00 mmol). Tetra-isopropoxytitanium(IV) was over 2 min under slight cooling added to the suspension. The reaction mixture was then stirred at rt overnight. At rt—after 17 hours—$NaBH_4$ was added (113 mg, 3.00 mmol). The suspension was then stirred at rt for another 6.5 hours before 2M aq ammonia (6 mL) was carefully added under cooling. The solid parts were removed by filtration and the filter cake was washed with dichloromethane (10 mL). The organic phase was isolated. The filter cake was once again washed with dichloromethane (10 mL). The combined filtrates were washed with water and then treated with 1M aq. HCl (5 mL). The acidic water phase was washed with dichloromethane (10 mL) before the pH was adjusted to ~11 by addition of 2M NaOH. The aqueous phase was then extracted with dichloromethane (3×10 mL). The combined organic phases were washed with brine, dried over sodium sulfate and filtered. Evaporation under reduced pressure (60 mbar/35° C.) afforded the title compound (268 mg, 83%) as colorless liquid.

$^1$H NMR (600 MHz, $CDCl_3$) δ 7.25-7.21 (m, 2H), 6.89-6.84 (m, 2H), 3.80 (s, 3H), 3.68 (s, 2H).

Step 2 trans-2-[4-[2-[(1R)-1-[tert-Butyl(dimethyl)silyl]oxyethyl]-6-[(4-methoxyphenyl)methyl-trideuteriomethyl-amino]imidazo[4,5-c]pyridin-1-yl]cyclohexyl] acetonitrile

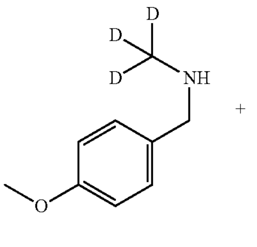

-continued

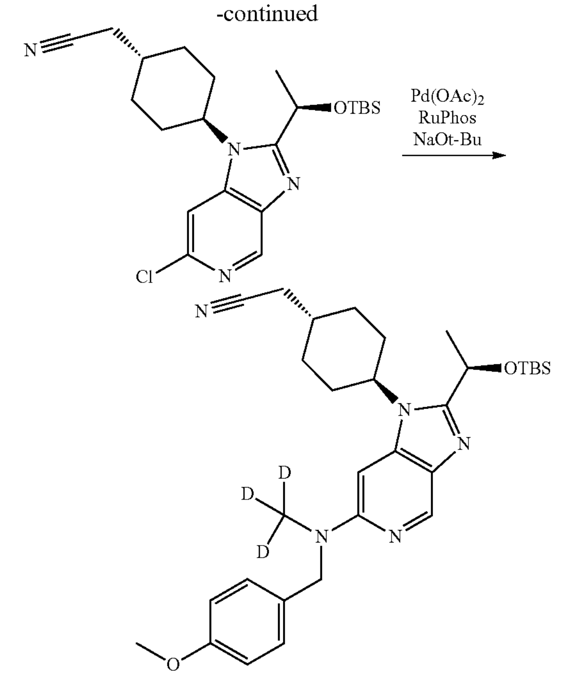

A 4 mL screwcap vial was charged with trans-2-[4-[2-[(1R)-1-[tert-butyl(dimethyl)silyl]oxyethyl]-6-chloro-imidazo[4,5-c]pyridin-1-yl]cyclohexyl]acetonitrile (150 mg, 0.346 mmol) and 1,1,1-trideuterio-N-[(4-methoxyphenyl) methyl]methanamin (107 mg, 0.693 mmol). The vial was flushed with argon, and a mixture of sodium tert-butoxide (40 mg, 0.416 mmol), RuPhos (9.7 mg, 0.021 mmol) and palladium(II) acetate (2.3 mg, 0.010 mmol) was added. The mixture was stirred under argon for 18 hours at 110° C. It was cooled to rt and a dichloromethane/EtOH 95:5 solution (1.5 mL) was added. The mixture was washed with brine: water 2:1 (1.2 mL) and the aqueous layer was extracted with a dichloromethane/EtOH 95:5 solution (2×1.5 mL). The combined organic layers were dried over $Na_2SO_4$, filtered and evaporated. Column chromatography (1% to 5% of MeOH in DCM as eluent) afforded the title compound and the corresponding des-TBS analogue (0.109 g) as yellow foam. This material was used in the next step without further purification.

Step 3 trans-2-[4-[2-[(1R)-1-Hydroxyethyl]-6-(trideuteriomethylamino)imidazo[4,5-c]pyridin-1-yl]cyclohexyl]acetonitrile

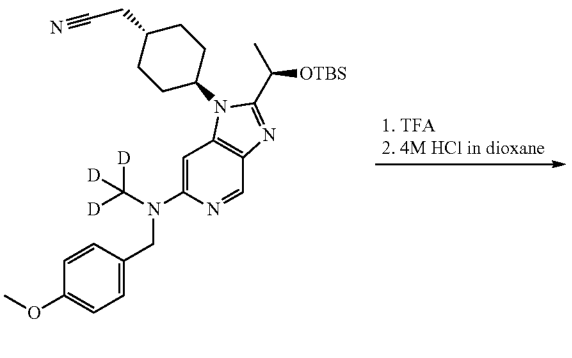

-continued

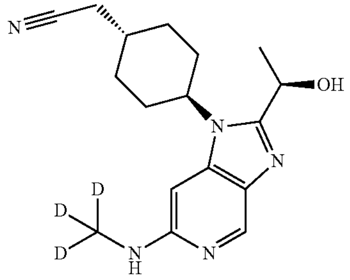 [SMILES: [2H]C([2H])([2H])Nc1cc2c(cn1)nc([C@@H](C)O)n2[C@H]1CC[C@H](CC#N)CC1]

The crude product from Step 2 was dissolved in TFA (0.75 mL) at 0° C. and the mixture was stirred at rt for 1.5 hours. Volatiles were removed under vacuum and the residue was at 0° C. dissolved in 4 M hydrogen chloride in dioxane (0.75 mL). The mixture was stirred at rt for 17 hours before volatiles were removed by evaporation. Water (0.5 mL) was added to the residue and the aqueous phase was washed with EtOAc (2×0.5 mL). The organic phases were washed with water (0.5 mL). The pH of the combined aqueous phases were adjusted to ~11 with sat. aq. sodium carbonate. The aqueous phase was then extracted with DCM:MeOH 95:5 (3×0.5 mL) and the combined organic phases were dried over $Na_2SO_4$, filtered and evaporated. Column chromatography (3% to 5% of MeOH in DCM as eluent) afforded the title compound (48 mg, 42%) as off-white foam.

UPLC-MS (Method B): $t_R$=0.38 min, m/z=317.3 ($M+H^+$).

$^1$H NMR (600 MHz, DMSO-$d_6$) δ 8.33 (br s, 1H), 6.47 (br s, 1H), 5.87 (s, 1H), 5.59 (d, J=6.8 Hz, 1H), 4.96 (p, J=6.5 Hz, 1H), 4.59-4.49 (m, 1H), 2.55 (d, J=6.3 Hz, 2H), 2.25-2.14 (m, 2H), 1.96-1.80 (m, 5H), 1.54 (d, J=6.5 Hz, 3H), 1.35-1.24 (m, 2H).

Example 5 trans-2-[4-[2-[1,2,2,2-Tetradeuterio-1-hydroxyethyl]-6-(methylamino)imidazo[4,5-c]pyridin-1-yl]cyclohexyl]acetonitrile (Compound 5)

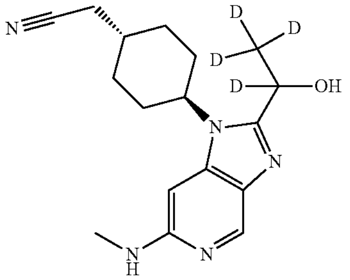 [SMILES: [2H]C([2H])([2H])C([2H])(O)c1nc2cnc(NC)cc2n1[C@H]1CC[C@H](CC#N)CC1]

Step 1 trans-2-[4-(2-Acetyl-6-chloro-imidazo[4,5-c]pyridin-1-yl)cyclohexyl]acetonitrile

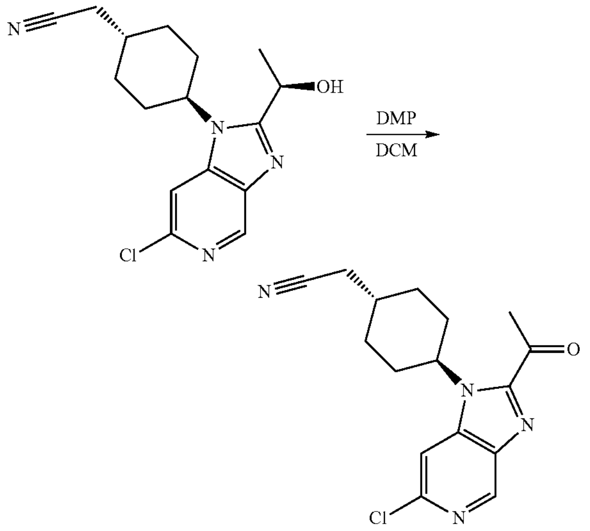

To a solution of 2-[trans-4-[6-chloro-2-[(1R)-1-hydroxyethyl]-1H-imidazo[4,5-c]pyridin-1-yl]cyclohexyl]acetonitrile (5.0 g, 15.6 mmol) in DCM (50 mL) was added DMP (10 g, 23.5 mmol) portion wise at 0° C. to 5° C. to RT. The reaction mixture was stirred at RT for 16 hours. On completion, the reaction mixture was filtered through celite bed and washed with DCM. The filtrate was washed with sat. $NaHCO_3$ (300 mL) and brine solution, dried over anhydrous $Na_2SO_4$, concentrated under reduced pressure and purified by silica gel (100-200 mesh) column chromatography (10 to 20% EtOAc in pet. ether as eluent) to afford the title compound (3.5 g, 71%) as an off-white solid.

LC-MS (Method D): $t_R$=1.84 min, m/z=316.11 ($M+H^+$).

$^1$H NMR (400 MHz, $CDCl_3$) δ 8.98 (s, 1H), 8.21 (s, 1H), 5.23-5.18 (m, 1H), 2.75 (s, 3H), 2.54 (d, J=6.5, 2H), 2.31-2.23 (m, 2H), 2.08-2.05 (m, 1H), 1.94-1.89 (m, 4H), 1.30-1.27 (m, 2H).

Step 2 trans-2-[4-[6-Chloro-2-(2,2,2-trideuterioacetyl)imidazo[4,5-c]pyridin-1-yl]cyclohexyl]acetonitrile

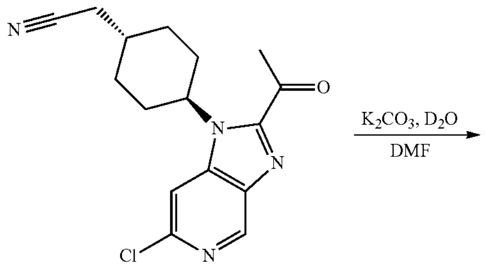

-continued

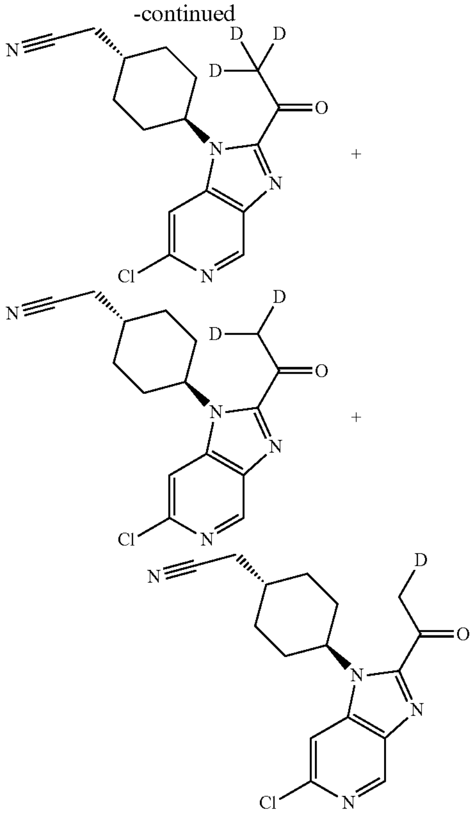

A suspension of trans-2-[4-(2-acetyl-6-chloro-imidazo[4,5-c]pyridin-1-yl)cyclohexyl]acetonitrile (3.5 g, 11.1 mmol) in DMF (35 mL) was added $K_2CO_3$ (4.5 g, 33.2 mmol) at RT and was subsequently stirred at that temperature for 16 hours. The reaction mixture was quenched with $D_2O$ (10 mL) and stirred at RT for 4 hours before ice-cold water was added. Ethyl acetate (70 mL) was added. The phases were separated. The aqueous phase was extracted with ethyl acetate (2x35 mL) and the combined organic phases were washed with brine, dried over anhydrous $Na_2SO_4$, concentrated under reduced pressure and purified by column chromatography using silica gel (100-200 mesh) (10 to 20% EtOAc in pet. ether as an eluent) to afford 2.5 g of the crude product as off white solid. The obtained material was a mixture of isotopomers. Based on $^1H$ NMR the distribution of isotopomers was; un-deuterated ($CH_3$): 7.6%, mono-deuterated ($CH_2D$): 26.33%, di-deuterated ($CHD_2$): 32.34% and tri-deuterated ($CD_3$): 33.72%

The above procedure was repeated with the obtained crude product to afford 1.8 g of a new crude product as an off-white solid. Based on $^1H$ NMR the distribution of isotopomers was; un-deuterated ($CH_3$): 0.66%, mono-deuterated ($CH_2D$): 4.47%, di-deuterated ($CHD_2$): 23.84% and tri-deuterated ($CD_3$): 71.02%

The above procedure was repeated once again with the obtained crude product to afford 1.2 g (35% overall yield) of the "title compound" as an off-white solid. Isotopic purity: 99.3%. Based on $^1H$ NMR the distribution of isotopomers was; un-deuterated ($CH_3$): 0.66%, mono-deuterated ($CH_2D$): 3.47%, di-deuterated ($CHD_2$): 21.85% and tri-deuterated ($CD_3$): 74.02%.

LC-MS (Method E): $t_R$=1.79 min, m/z=320.19 (M+H$^+$).

$^1H$ NMR (400 MHz, $CDCl_3$) δ 8.98 (s, 1H), 7.54 (s, 1H), 5.40-5.45 (m, 1H), 2.39 (d, J=6.5, 2H), 2.27-2.219 (m, 2H), 2.13-2.04 (m, 4H), 1.96-1.90 (m, 1H), 1.45-1.39 (m, 2H).

Step 3 trans-2-[4-[6-Chloro-2-(1,2,2,2-tetradeuterio-1-hydroxy-ethyl)imidazo[4,5-c]pyridin-1-yl]cyclohexyl]acetonitrile

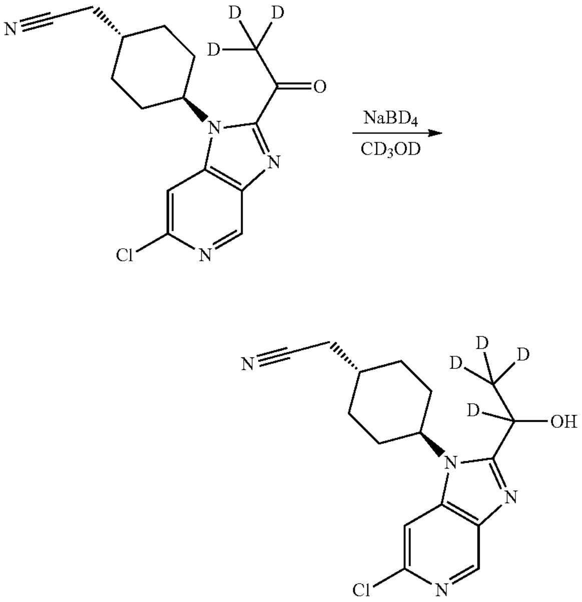

A suspension of trans-2-[4-[6-chloro-2-(2,2,2-trideuterio-acetyl)imidazo[4,5-c]pyridin-1-yl]cyclohexyl]acetonitrile (1.5 g, 4.69 mmol) in $CD_3OD$ (15 mL) was added $NaBD_4$ (0.29 g, 7.04 mmol) at 0° C. to 5° C. The reaction mixture was stirred at RT for 1 hour. On completion, reaction was quenched with $D_2O$ and the mixture was concentrated under reduced pressure. The crude compound was dissolved in the $H_2O$ and extracted with 10% MeOH in DCM (2x15 mL). The combined organic layer was washed with brine, dried over anhydrous $Na_2SO_4$, concentrated under reduced pressure and purified by silica gel (100-200 mesh) column chromatography (1 to 3% MeOH in DCM as an eluent) to afford the title compound (1.2 g, 80%) as an off-white solid. Obtained compound was a mixture of isotopomers. Based on $^1H$ NMR the distribution of isotopomers was; mono-deuterated ($CDOHCH_3$): 0.66%, di-deuterated ($CDOHCH_2D$): 3.47%, tri-deuterated ($CDOHCHD_2$): 21.85% and tetra-deuterated ($CDOHCD_3$): 74.02%.

LC-MS (Method E): $t_R$=1.48 min, m/z=323.23 (M+H$^+$).

$^1H$ NMR (400 MHz, $CDCl_3$) δ 8.69 (s, 1H), 8.01 (s, 1H), 5.77 (s, 1H), 4.68-4.63 (m, 1H), 2.54 (d, J=6, 2H), 2.27-2.21 (m, 2H), 2.10-2.08 (m, 1H), 1.93-1.86 (m, 4H), 1.32-1.26 (m, 2H).

Step 4 trans-2-[4-[2-[1,2,2,2-Tetradeuterio-1-hydroxyethyl]-6-(methylamino)imidazo[4,5-c]pyridin-1-yl]cyclohexyl]acetonitrile

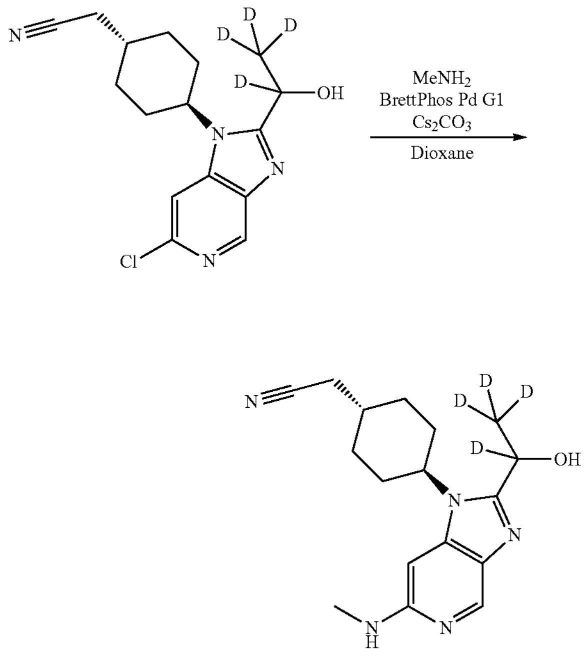

In a sealed tube, a solution of trans-2-[4-[6-chloro-2-(1,2,2,2-tetradeuterio-1-hydroxy-ethyl)imidazo[4,5-c]pyridin-1-yl]cyclohexyl]acetonitrile (0.10 g, 0.309 mmol) in degassed 1,4-dioxane (5.0 mL) was added $Cs_2CO_3$ (0.302 g, 0.927 mmol), Brettphos Pd G1 (0.037 g, 0.046 mmol) and purged with argon for 10 minutes, before 2M $CH_3NH_2$ in THF (0.60 mL, 1.24 mmol) was added. The reaction mixture was stirred at 80° C. for 16 hours. On completion, the reaction mixture was cooled to RT and filtered through a Celite pad and washed with EtOAc. The filtrate was concentrated under reduced pressure. The obtained residue was taken in water and extracted twice with DCM (2×10 mL). The combined organic phases were washed with brine, dried over anhydrous $Na_2SO_4$ and concentrated under reduced pressure. The crude product was purified by silica gel (100-200 mesh) column chromatography (3% of MeOH in DCM as eluent) to afford the title compound (0.04 g, 41%) as light brown solid.

LC-MS (Method E): $t_R$=1.14 min, m/z=318 (M+H$^+$).

Estimated deuterium isotopic distribution in molar %: $D_0$, $D_1$, $D_2$, $D_3$, $D_4$=0, 0, 3, 21, 76.

$^1$H NMR (400 MHz, DMSO-$d_6$): δ (ppm) 8.32 (s, 1H), 6.47 (s, 1H), 5.93-5.89 (m, 1H), 5.58 (s, 1H), 4.57-4.51 (m, 1H), 2.78 (d, J=5.2 Hz, 3H), 2.55 (d, J=6.4 Hz, 2H), 2.24-2.17 (m, 2H), 1.94-1.86 (m, 5H), 1.31-1.23 (m, 2H).

Example 6 cis-2-[4-[2-[1-Hydroxyethyl]-6-(methylamino)imidazo[4,5-c]pyridin-1-yl]cyclohexyl]acetonitrile (Compound 6)

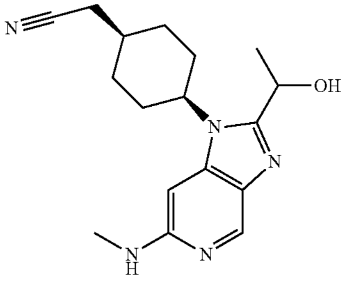 [SMILES: CNc1cc2c(cn1)nc(C(C)O)n2[C@H]1CC[C@@H](CC#N)CC1]

cis-2-[4-[2-[1-Hydroxyethyl]-6-(methylamino)imidazo[4,5-c]pyridin-1-yl]cyclohexyl]acetonitrile was obtained following a small scale procedure similar to the one outlined in the “Alternative preparation no 2” of Example 3 with the only major differences being that in Step 1 trans-4-(cyanomethyl)cyclohexyl]ammonium hydrochloride was replaced by cis-4-(cyanomethyl)cyclohexyl]ammonium hydrochloride (CAS Registry Number 1461718-40-0) and that (R)-lactamide was replaced by lactamide in Step 3.

UPLC-MS (Method C): $t_R$=1.62 min, m/z=314.4 (M+H$^+$).

$^1$H NMR (400 MHz, DMSO-$d_6$) δ 8.34 (s, 1H), 6.51 (s, 1H), 5.97-5.88 (m, 1H), 5.56 (d, J=6.8 Hz, 1H), 4.95 (p, J=6.5 Hz, 1H), 4.60-4.46 (m, 1H), 2.85-2.77 (m, 5H), 2.27-2.08 (m, 3H), 1.89-1.62 (m, 6H), 1.54 (d, J=6.5 Hz, 3H).

Example 7 cis-2-[4-[2-[(1R)-1-Hydroxyethyl]-6-(methylamino)imidazo[4,5-c]pyridin-1-yl]cyclohexyl]acetonitrile (Compound 7)

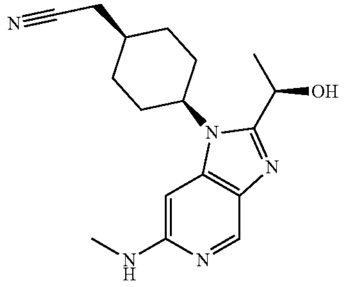 [SMILES: CNc1cc2c(cn1)nc([C@@H](C)O)n2[C@H]1CC[C@@H](CC#N)CC1]

cis-2-[4-[2-[(1R)-1-Hydroxyethyl]-6-(methylamino)imidazo[4,5-c]pyridin-1-yl]cyclohexyl]acetonitrile was obtained following a small scale procedure similar to the one outlined in the “Alternative preparation no. 2” of Example 3 with the only major difference being that trans-4-(cyanomethyl)cyclohexyl]ammonium hydrochloride was replaced by cis-4-(cyanomethyl)cyclohexyl]ammonium hydrochloride (CAS Registry Number 1461718-40-0) in the first step of the reaction sequence.

UPLC-MS (Method C): $t_R$=1.62 min, m/z=314.4 (M+H$^+$).

$^1H$ NMR (400 MHz, DMSO-$d_6$) δ 8.35 (s, 1H), 6.53 (s, 1H), 5.98 (br s, 1H), 5.58 (d, J=6.7 Hz, 1H), 4.95 (p, J=6.5 Hz, 1H), 4.60-4.46 (m, 1H), 2.86-2.76 (m, 5H), 2.27-2.07 (m, 3H), 1.89-1.62 (m, 6H), 1.54 (d, J=6.5 Hz, 3H).

Example 8 trans-2-[4-[2-[(1R)-1-Hydroxyethyl]-6-(methylamino)imidazo[4,5-c]pyridin-1-yl]cyclohexyl]acetonitrile malonic acid salt (Compound 8)

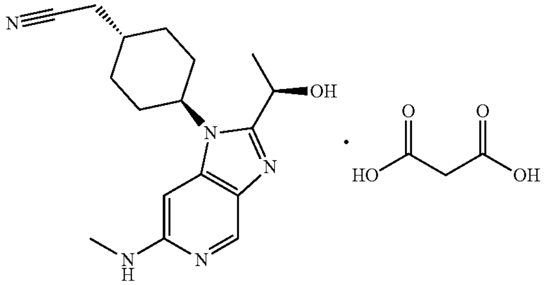 [SMILES: CNc1cc2c(cn1)nc([C@@H](C)O)n2[C@H]1CC[C@H](CC#N)CC1 ; O=C(O)CC(=O)O]

trans-2-[4-[2-[(1R)-1-Hydroxyethyl]-6-(methylamino)imidazo[4,5-c]pyridin-1-yl]cyclohexyl]acetonitrile (1.40 g, 4.46 mmol) was dissolved in isopropanol (50 mL) at 45° C. Malonic acid (232 mg, 2.23 mmol) in isopropanol (5.0 mL) was added. The volume of the reaction mixture was reduced by evaporation under reduced pressure at 45° C. (~30 mL of isopropanol was distilled off). Addition of a few reference crystals of the title compound initiated the crystallization. The volume of the reaction mixture was further reduced by evaporation under reduced pressure (~15 mL of isopropanol was distilled off). The obtained suspension was cooled in an ice bath and after a while the solid was filtered off and washed with ice cold isopropanol (3×2 mL). Drying under reduced pressure afforded the title compound (932 mg, ~100%) as off-white crystals.

$^1H$ NMR (600 MHz, DMSO-$d_6$) δ 8.37 (s, 1H), 6.54 (s, 1H), 6.10 (br s, 1H), 5.66 (br s, 1H), 4.98 (q, J=6.5 Hz, 1H), 4.62-4.51 (m, 1H), 3.17 (s, 2H), 2.81 (s, 3H), 2.55 (d, J=6.3 Hz, 2H), 2.25-2.14 (m, 2H), 1.97-1.81 (m, 5H), 1.55 (d, J=6.5 Hz, 3H), 1.36-1.24 (m, 2H).

M.p. (DSC onset temperature) 109±2° C.

Example 9 trans-2-[4-[2-[(1R)-1-Hydroxyethyl]-6-(methylamino)imidazo[4,5-c]pyridin-1-yl]cyclohexyl]acetonitrile glycolic acid salt (Compound 9)

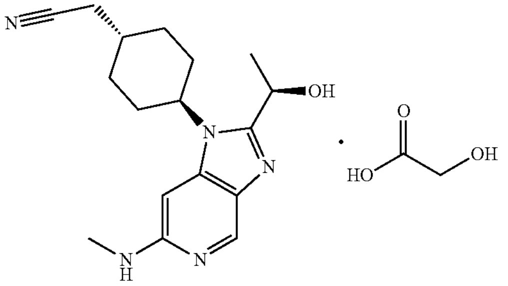 [SMILES: CNc1cc2c(cn1)nc([C@@H](C)O)n2[C@H]1CC[C@H](CC#N)CC1 ; O=C(O)CO]

trans-2-[4-[2-[(1R)-1-Hydroxyethyl]-6-(methylamino)imidazo[4,5-c]pyridin-1-yl]cyclohexyl]acetonitrile (1.80 g, 5.74 mmol) was dissolved in isopropanol (65 mL) at 45° C. Glycolic acid (437 mg, 5.74 mmol) in isopropanol (8.0 mL) was added. The volume of the reaction mixture was reduced by evaporation under reduced pressure at 45° C. (~65 mL of isopropanol was distilled off). Addition of a few reference crystals of the title compound slowly initiated the crystallization. EtOAc (15 mL) was added. The obtained suspension was cooled in an ice bath and after a while the solid was filtered off and washed with an ice cold 9:1 mixture of EtOAc:isopropanol (2×2 mL). Drying under reduced pressure afforded the title compound (1.57 g, 70%) as off-white crystals.

$^1H$ NMR (600 MHz, DMSO-$d_6$) δ 8.33 (s, 1H), 6.47 (s, 1H), 5.90 (br s, 1H), 5.58 (d, J=6.6 Hz, 1H), 4.96 (p, J=5.3 Hz, 1H), 4.59-4.51 (m, 1H), 3.90 (s, 2H), 2.79 (s, 3H), 2.55 (d, J=6.2 Hz, 2H), 2.25-2.14 (m, 2H), 1.97-1.80 (m, 5H), 1.54 (d, J=6.4 Hz, 3H), 1.36-1.25 (m, 2H).

M.p. (DSC onset temperature) 100±2° C.

Example 10 trans-2-[4-[2-[(1R)-1-Hydroxyethyl]-6-(methylamino)imidazo[4,5-c]pyridin-1-yl]cyclohexyl]acetonitrile L-tartaric acid salt (Compound 10)

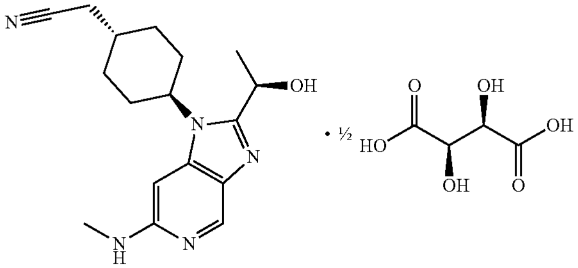 [SMILES: CNc1cc2c(cn1)nc([C@@H](C)O)n2[C@H]1CC[C@H](CC#N)CC1 ; O=C(O)[C@H](O)[C@@H](O)C(=O)O]

trans-2-[4-[2-[(1R)-1-Hydroxyethyl]-6-(methylamino)imidazo[4,5-c]pyridin-1-yl]cyclohexyl]acetonitrile (1.50 g, 4.79 mmol) was dissolved in methanol (25 mL) at 45° C. L-Tartaric acid (360 mg, 2.40 mmol) in methanol (10 mL) was added. The volume of the reaction mixture was reduced by evaporation under reduced pressure at 45° C. (~10 mL of methanol was distilled off). Addition of a few reference crystals of the title compound initiated the crystallization. Isopropanol (30 mL) was added and the volume of the reaction mixture was reduced by evaporation under reduced pressure at 45° C. (~20 mL was distilled off). The obtained suspension was cooled in an ice bath and after a while the solid was filtered off and washed with ice cold isopropanol (4×4 mL). Drying under reduced pressure afforded the title compound (1.55 g, 83%) as off-white crystals.

$^1H$ NMR (600 MHz, DMSO-$d_6$) δ 8.34 (s, 1H), 6.49 (s, 1H), 5.98 (br s, 1H), 5.60 (br s, 1H), 4.96 (q, J=6.4 Hz, 1H), 4.60-4.49 (m, 1H), 4.28 (s, 1H), 2.80 (s, 3H), 2.55 (d, J=6.3 Hz, 2H), 2.26-2.13 (m, 2H), 1.97-1.80 (m, 5H), 1.54 (d, J=6.5 Hz, 3H), 1.36-1.25 (m, 2H).

M.p. (DSC onset temperature) 98±2° C.

Example 11 trans-2-[4-[2-[(1R)-1-Hydroxyethyl]-6-(methylamino)imidazo[4,5-c]pyridin-1-yl]cyclohexyl]acetonitrile L-malic acid salt (Compound 11)

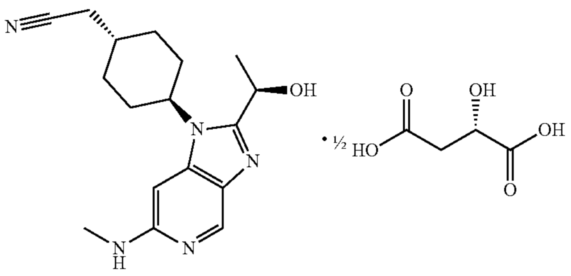 [SMILES: CNc1cc2c(cn1)nc([C@@H](C)O)n2[C@H]1CC[C@H](CC#N)CC1 ; O=C(O)C[C@H](O)C(=O)O]

trans-2-[4-[2-[(1R)-1-Hydroxyethyl]-6-(methylamino)imidazo[4,5-c]pyridin-1-yl]cyclohexyl]acetonitrile (1.50 g, 4.79 mmol) was dissolved in methanol (25 mL) at 45° C. L-Malic acid (332 mg, 2.40 mmol) in methanol (10 mL) was added. The volume of the reaction mixture was reduced by evaporation under reduced pressure at 45° C. (~20 mL of methanol was distilled off). Addition of a few reference crystals of the title compound initiated the crystallization. Isopropanol (30 mL) was added and the volume of the reaction mixture was reduced by evaporation under reduced pressure at 45° C. (~10 mL was distilled off). The obtained suspension was cooled in an ice bath and after a while the solid was filtered off and washed with ice cold isopropanol (4×4 mL). Drying under reduced pressure afforded the title compound (1.51 g, 79%) as off-white crystals.

$^1$H NMR (600 MHz, DMSO-$d_6$) δ 8.34 (s, 1H), 6.49 (s, 1H), 5.95 (br s, 1H), 5.59 (d, J=6.7 Hz, 1H), 4.96 (p, J=6.5 Hz, 1H), 4.59-4.51 (m, 1H), 4.23 (dd, J=7.5, 5.3 Hz, 0.5H), 2.79 (s, 3H), 2.60 (dd, J=15.6, 5.3 Hz, 0.5H), 2.55 (d, J=6.4 Hz, 2H), 2.43 (dd, J=15.6, 7.5 Hz, 0.5H), 2.25-2.14 (m, 2H), 1.96-1.81 (m, 5H), 1.54 (d, J=6.5 Hz, 3H), 1.36-1.25 (m, 2H).

M.p. (DSC onset temperature) 94° C.±2° C.

Example 12 trans-2-[4-[2-[(1R)-1-Hydroxyethyl]-6-(methylamino)imidazo[4,5-c]pyridin-1-yl]cyclohexyl]acetonitrile sulfuric acid salt (Compound 12)

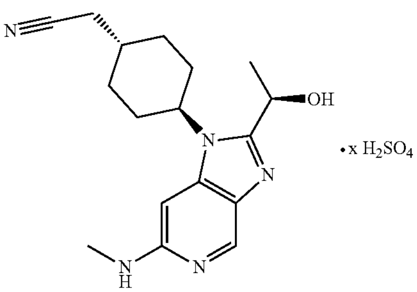

Unknown stoichiometry trans-2-[4-[2-[(1R)-1-Hydroxyethyl]-6-(methylamino)imidazo[4,5-c]pyridin-1-yl]cyclohexyl]acetonitrile (1.50 g, 4.79 mmol) was dissolved in methanol (10 mL) at 45° C. Sulfuric acid (1.0 M, 4.79 mL, 4.79 mmol) in isopropanol (5.0 mL) was added. The volume of the reaction mixture was reduced by evaporation under reduced pressure at 45° C. (~7 mL was distilled off). Addition of a few reference crystals of the title compound initiated the crystallization. The obtained suspension was cooled in an ice bath and after a while the solid was filtered off and washed with ice cold isopropanol (2×2 mL). Drying under reduced pressure afforded the title compound (1.57 g) as off-white crystals.

$^1$H NMR (600 MHz, DMSO-$d_6$) δ 13.32 (br s, 1H), 8.61 (s, 1H), 7.49 (br s, 1H), 6.95 (s, 1H), 5.91 (br s, 1H), 5.07 (q, J=6.5 Hz, 1H), 4.67-4.58 (m, 1H), 2.96 (s, 3H), 2.56 (d, J=6.0 Hz, 2H), 2.26-2.14 (m, 2H), 1.99-1.87 (m, 5H), 1.57 (d, J=6.5 Hz, 3H), 1.38-1.27 (m, 2H).

M.p. (DSC onset temperature) 169±2° C.

Example 13 trans-2-[4-[2-[(1R)-1-Hydroxyethyl]-6-(methylamino)imidazo[4,5-c]pyridin-1-yl]cyclohexyl]acetonitrile hydrochloric acid salt (Compound 13)

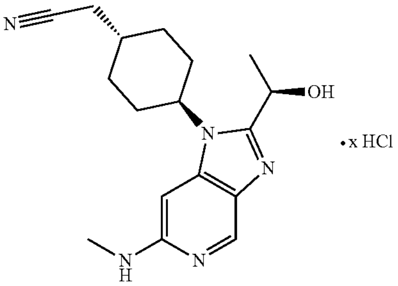

Unknown stoichiometry trans-2-[4-[2-[(1R)-1-Hydroxyethyl]-6-(methylamino)imidazo[4,5-c]pyridin-1-yl]cyclohexyl]acetonitrile (2.00 g, 6.38 mmol) was dissolved in isopropanol (70 mL) at 45° C. Methanolic hydrochloric acid (3.0 M, 6.38 mL, 19.1 mmol) was added at rt. The volume of the reaction mixture was reduced by evaporation under reduced pressure at 45° C. (~45 mL was distilled off). Addition of a few reference crystals of the title compound initiated the crystallization. The volume of the reaction mixture was further reduced by evaporation under reduced pressure (~5 mL was distilled off). The obtained suspension was cooled in an ice bath and after a while the solid was filtered off and washed with ice cold isopropanol (4×4 mL). Drying under reduced pressure afforded the title compound (1.30 g) as off-white crystals.

$^1$H NMR (600 MHz, DMSO-$d_6$) δ 14.06 (br s, 1H), 8.60 (s, 1H), 7.84 (br s, 1H), 7.02 (s, 1H), 6.16 (br s, 1H), 5.07 (q, J=6.5 Hz, 1H), 4.69-4.60 (m, 1H), 2.98 (s, 3H), 2.56 (d, J=6.0 Hz, 2H), 2.27-2.16 (m, 2H), 2.01-1.86 (m, 5H), 1.57 (d, J=6.5 Hz, 3H), 1.39-1.28 (m, 2H).

M.p. (DSC onset temperature) 148±2° C.

Example 14 trans-2-[4-[2-[(1R)-1-Hydroxyethyl]-6-(methylamino)imidazo[4,5-c]pyridin-1-yl]cyclohexyl]acetonitrile succinic acid salt (Compound 14)

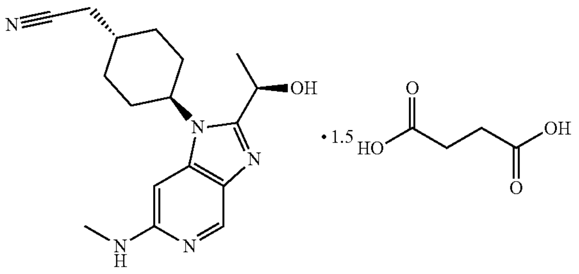 [SMILES: CNc1cc2c(cn1)nc([C@@H](C)O)n2[C@H]1CC[C@H](CC#N)CC1 ; O=C(O)CCC(=O)O]

trans-2-[4-[2-[(1R)-1-Hydroxyethyl]-6-(methylamino) imidazo[4,5-c]pyridin-1-yl]cyclohexyl]acetonitrile (31.3 mg, 0.100 mmol) was dissolved in ethanol (0.20 mL) at ~50° C. Succinic acid (11.8 mg, 0.100 mmol) in ethanol (0.25 mL) was added. The volume of the reaction mixture was reduced by evaporation under reduced pressure at 45° C. (~0.14 mL of ethanol was distilled off). After crystallization had occurred ethanol (0.10 mL) was added. The obtained suspension was cooled in an ice bath and after a while filtration afforded the title compound (16 mg, 33%) as off-white crystals.

$^1$H NMR (600 MHz, DMSO-$d_6$) δ 12.16 (br s, 3H), 8.33 (s, 1H), 6.48 (s, 1H), 5.91 (br s, 1H), 5.59 (d, J=6.7 Hz, 1H), 4.96 (p, J=6.5 Hz, 1H), 4.59-4.50 (m, 1H), 2.79 (s, 3H), 2.55 (d, J=6.3 Hz, 2H), 2.42 (s, 6H), 2.25-2.14 (m, 2H), 1.97-1.80 (m, 5H), 1.54 (d, J=6.5 Hz, 3H), 1.35-1.24 (m, 2H).

M.p. (DSC onset temperature) 162±2° C.

Example 15 trans-2-[4-[2-[(1R)-1-Hydroxyethyl]-6-(methylamino)imidazo[4,5-c]pyridin-1-yl]cyclohexyl]acetonitrile oxalic acid salt (Compound 15)

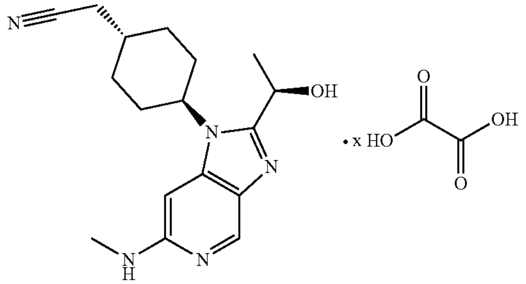

Unknown stoichiometry trans-2-[4-[2-[(1R)-1-Hydroxyethyl]-6-(methylamino) imidazo[4,5-c]pyridin-1-yl]cyclohexyl]acetonitrile (31.3 mg, 0.100 mmol) was dissolved in ethanol (0.20 mL) at ~50° C. Oxalic acid (4.5 mg, 0.050 mmol) in ethanol (0.25 mL) was added. The reaction mixture was cooled in an ice bath and after a while filtration afforded the title compound (27 mg) as off-white crystals.

$^1$H NMR (600 MHz, DMSO-$d_6$) δ 8.39 (s, 1H), 6.57 (s, 1H), 4.98 (q, J=6.5 Hz, 1H), 4.60-4.52 (m, 1H), 2.83 (s, 3H), 2.55 (d, J=6.3 Hz, 2H), 2.25-2.14 (m, 2H), 1.97-1.82 (m, 5H), 1.55 (d, J=6.4 Hz, 3H), 1.36-1.25 (m, 2H).

M.p. (DSC onset temperature) 134±2° C.

Example 16 trans-2-[4-[2-[(1R)-1-Hydroxyethyl]-6-(methylamino)imidazo[4,5-c]pyridin-1-yl]cyclohexyl]acetonitrile fumaric acid salt (Compound 16)

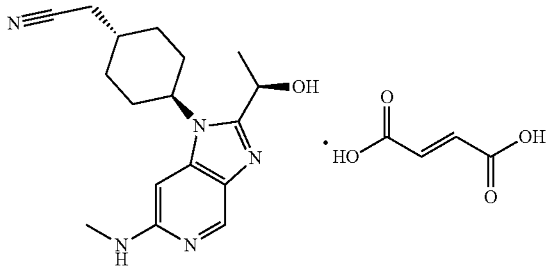 [SMILES: CNc1cc2c(cn1)nc([C@@H](C)O)n2[C@H]1CC[C@H](CC#N)CC1 ; O=C(O)/C=C/C(=O)O]

trans-2-[4-[2-[(1R)-1-Hydroxyethyl]-6-(methylamino) imidazo[4,5-c]pyridin-1-yl]cyclohexyl]acetonitrile (3.00 g, 9.57 mmol) was dissolved in ethanol (6.0 mL). Fumaric acid (1.11 g, 9.57 mmol) dissolved at ~50° C. in ethanol (12 mL) was added slowly. A crystallization occurred. The obtained suspension was allowed to reach rt and after a while the solid was filtered off and washed with ethanol (2×0.5 mL). Drying under reduced pressure afforded the title compound (3.26 g, 79%) as off-white crystals 1H NMR (600 MHz, DMSO-$d_6$) δ 8.34 (s, 1H), 6.63 (s, 2H), 6.49 (s, 1H), 4.97 (q, J=6.5 Hz, 1H), 4.60-4.51 (m, 1H), 2.80 (s, 3H), 2.55 (d, J=6.3 Hz, 2H), 2.26-2.14 (m, 2H), 1.97-1.80 (m, 5H), 1.54 (d, J=6.5 Hz, 3H), 1.35-1.24 (m, 2H).

M.p. (DSC onset temperature) 111±2° C.

Example 17 trans-2-[4-[2-[(1R)-1-Hydroxyethyl]-6-(methylamino)imidazo[4,5-c]pyridin-1-yl]cyclohexyl]acetonitrile 1,5-naphthalenedisulfonic acid salt (Compound 17)

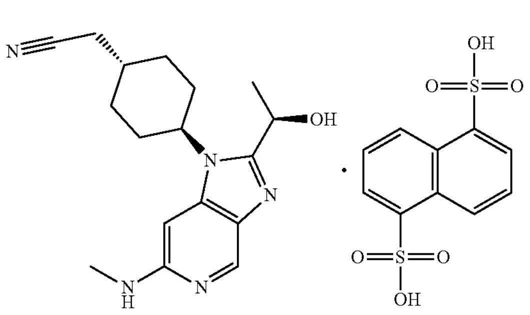

trans-2-[4-[2-[(1R)-1-Hydroxyethyl]-6-(methylamino) imidazo[4,5-c]pyridin-1-yl]cyclohexyl]acetonitrile acetonitrile (11.8 mg, 0.037 mmol) was dissolved in ethyl acetate (1 mL) at ~50° C. 1,5-naphthalenedisulfonic acid (tetra hydrate) (15.0 mg, 0.042 mmol) in $H_2O$ (150 μL) was added. The solution was stirred very slowly at a magnet stirring unit for approximate 3 days, whereupon off-white crystals were isolated by filtration.

$^1$H NMR (600 MHz, DMSO-$d_6$) δ 8.88 (d, J=8.5 Hz, 2H), 8.60 (s, 1H), 7.95 (dd, J=7.1, 1.2 Hz, 2H), 7.54 (br s, 1H), 7.42 (dd, J=8.5, 7.1 Hz, 2H), 6.97 (s, 1H), 5.06 (q, J=6.5 Hz, 1H), 4.63-4.56 (m, 3H), 2.95 (s, 3H), 2.51 (d, J=5.4 Hz, 2H), 2.28-2.06 (m, 2H), 1.95-1.72 (m, 5H), 1.56 (d, J=6.5 Hz, 3H), 1.38-1.18 (m, 2H).

M.p. (DSC onset temperature) 110±2° C.

Example 18 trans-2-[4-[2-[(1R)-1-Hydroxyethyl]-6-(methylamino)imidazo[4,5-c]pyridin-1-yl]cyclohexyl]acetonitrile DL-mandelic acid salt (Compound 18)

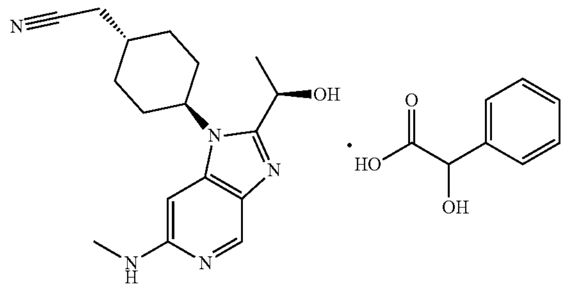 [SMILES: CNc1cc2c(cn1)nc([C@@H](C)O)n2[C@H]1CC[C@H](CC#N)CC1 ; O=C(O)C(O)c1ccccc1]

trans-2-[4-[2-[(1R)-1-Hydroxyethyl]-6-(methylamino) imidazo[4,5-c]pyridin-1-yl]cyclohexyl]acetonitrile acetonitrile (9.92 mg, 0.032 mmol) and DL-mandelic acid (5.3 mg, 0.035 mmol) were dissolved in ethyl acetate (1 mL) at ~50° C. The solution was stirred very slowly at a magnet stirring unit for approximate 3 days, whereupon off-white crystals were isolated by filtration.

$^1$H NMR (600 MHz, DMSO-$d_6$) δ 8.33 (d, J=0.9 Hz, 1H), 7.45-7.37 (m, 2H), 7.37-7.31 (m, 2H), 7.31-7.25 (m, 1H), 6.48 (d, J=1.0 Hz, 1H), 5.92 (br s, 1H), 5.59 (br s, 1H), 5.00 (s, 1H), 4.96 (q, J=6.8 Hz, 1H), 4.63-4.47 (m, 1H), 2.79 (s, 3H), 2.55 (d, J=6.4 Hz, 2H), 2.27-2.11 (m, 2H), 1.97-1.75 (m, 5H), 1.54 (d, J=6.5 Hz, 3H), 1.38-1.21 (m, 2H).

M.p. (DSC onset temperature) 153±2° C.

Example 19 trans-2-[4-[2-[(1R)-1-Hydroxyethyl]-6-(methylamino)imidazo[4,5-c]pyridin-1-yl]cyclohexyl]acetonitrile dioxane solvate (Compound 19)

A suspension of approx. 15 mg of trans-2-[4-[2-[(1R)-1-hydroxyethyl]-6-(methylamino)imidazo[4,5-c]pyridin-1-yl] cyclohexyl]acetonitrile in 0.4 mL of a 1,4-dioxane:heptane (1:1) mixture was made in a capped 2.5 mL vial equipped with a small magnet bar. The vial was placed at a magnet stirring unit and stirred at approximately 600 rpm for two weeks at r.t. The solid material was isolated by filtration and dried before melting point determination.

M.p. (DSC onset temperature) 77±2° C.

JAK Kinase Assays

Human baculovirus-expressed Janus kinase (JAK) 1, 2, 3 and tyrosin kinase (TYK) 2 were purchased from Carna Biosciences, Inc (#08-144, -045, -046, -147 resp.). All four purified enzymes contain only the catalytic domain. JAK1 (aa 850-1154) and TYK2 (aa 871-1187) are expressed with an N-terminally fused GST-tag, and JAK2 and JAK3 with an N-terminally fused His-tag. Inhibition of phosphorylation of a synthetic peptide was measured in an HTRF-based assay (CisBio #62TKOPEC). First, 75 nL of test compound solution (100% DMSO) was added to a white shallow 384-well plate (NUNC #264706) using a Labcyte ECHO 550 liquid handler. Thereafter, 1 μL of compound dilution buffer (50 mM HEPES, 0.05% bovine serum albumin) and 2 μL of TK solution (TK substrate-biotin in kinase buffer [1× enzymatic buffer from HTRFKinEASE TK kit, 1 mM DTT]) was added. Then, 5 μL kinase-ATP mix (prepared in kinase buffer) was added to the wells and the plates were incubated at RT for 20 (JAK2, 3 and TYK2) to 40 (JAK1) min. For all four kinases a concentration of ATP that corresponded to the $K_m$ for ATP was used. The final concentrations of buffers, substrate, kinase and ATP were: JAK1: 50 mM Hepes buffer pH 7.0, 0.01% BSA, 10 mM $MgCl_2$, 1 mM DTT, 7 μM ATP, 50 nM SEB, 1 μM TK Substrate-Biotin and 5 ng/well JAK1; JAK2: 50 mM Hepes buffer pH 7.0, 0.01% BSA, 5 mM $MgCl_2$, 1 mM DTT, 4 μM ATP, 1 μM TK Substrate-Biotin and 0.1 ng/well JAK2; JAK3: 50 mM Hepes buffer pH 7.0, 0.01% BSA, 5 mM $MgCl_2$, 1 mM DTT, 2 μM ATP, 1 μM TK Substrate-Biotin and 0.3 ng/well JAK3; TYK2: 50 mM Hepes buffer pH 7.0, 0.01% BSA, 5 mM $MgCl_2$, 1 mM DTT, 13 μM ATP, 50 nM SEB, 1 μM TK Substrate-Biotin and 0.8 ng/well TYK2. Thereafter, the kinase reaction was stopped by adding 4 μL detection mix (final concentrations: 50 mM Hepes buffer pH 7.0, 0.01% BSA, 0.8 M KF, 20 mM EDTA, 42 nM Streptavidin-XL665 and 1:400 STK Ab Cryptate) and the plates were incubated overnight in the dark. A PerkinElmer Envision reader was used to quantify the HTRF signal using the following filters; 320 nm excitation filter, 665 nm emission filter and a 615 nm $2^{nd}$ emission filter. A ratio ((665/615)×$10^4$) was calculated for each well.

STAT6 Assay

Twenty-five μL of a STAT6 bla-RA1 (Invitrogen # K1243) cell suspension was seeded with a density of 30-40,000 cells/well in 384-well Black View-plates (PerkinElmer #6007460) with clear bottom in assay medium (Opti-MEM (Invitrogen #11058-021)+0.5% heat inactivated fetal bovine Serum (Invitrogen #10082-147)+1% non-essential amino acids (Invitrogen #11140-050)+1% sodium pyruvate (Invitrogen #11360-070)+1% penicillin/streptomycin (Invitrogen #15140-122)); containing 550 ng/mL of CD40 ligand (Invitrogen # PHP0025). The cell plates were incubated overnight in a humidified 37° C. air/$CO_2$ (95%/5%) incubator. The following day, 125 nL of solutions of test compounds and reference compounds were transferred to cell plates using the Labcyte Echo 550 liquid handler. The plates were then incubated for 1 h in a humidified 37° C. air/$CO_2$ (95%/5%) incubator. Hereafter recombinant human interleukin 4 (Invitrogen # PHC0045) were added to the plates also using the Labcyte Echo 550 to a final concentration of 10 ng/mL. The cells were then incubated for 4½-5 h in a humidified 37° C. air/$CO_2$ (95%/5%) incubator. 8 μL of LiveBLAzer substrate mixture (Invitrogen # K1095) were then added to the assay plates, which were incubated overnight at RT. Fluorescence was then measured: Excitation: 405 nm; Emission: 460 nm (green channel), Emission: 535 nm (blue channel). Background was subtracted in both emission channels and the ratio 460/535 nm was calculated for each well.

STAT5 Assay

Twenty-five μL of a STAT5 irfl-bla TF1 (Invitrogen # K1219) cell suspension was seeded with a density of about 10,000 cells/well in 384-well Black View-plates (PerkinElmer #6007460) with clear bottom in assay medium (Opti-MEM (Invitrogen #11058-021)+0.5% heat inactivated fetal bovine Serum (Invitrogen #10082-147)+1% non-essential amino acids (Invitrogen #11140-050)+1% sodium pyruvate (Invitrogen #11360-070)+1% penicillin/streptomycin (Invitrogen #15140-122)). The cell plates were incubated overnight in a humidified 37° C. air/$CO_2$ (95%/5%) incubator. The following day, 125 nL of solutions of test compounds and reference compounds were transferred to cell plates using the Labcyte Echo 550 liquid handler. The plates were then incubated for 1 h in a humidified 37° C. air/$CO_2$ (95%/5%) incubator. Hereafter recombinant human erythropoietin (EPO) (Invitrogen # PHC9634) was added to the plates also using the Labcyte Echo 550 to a final concentration of 10 ng/mL. The cells were then incubated for 4½-5 h in a humidified 37° C. air/$CO_2$ (95%/5%) incubator. 8 μL of LiveBLAzer substrate mixture (Invitrogen # K1095) were then added to the assay plates, which were then incubated overnight at RT. Fluorescence was then measured: Excitation: 405 nm; Emission: 460 nm (green channel), Emission: 535 nm (blue channel). Background was subtracted in both emission channels and the ratio 460/535 nm was calculated for each well.

The compounds of the invention were tested in the JAK1, JAK2, JAK3 and TYK2 kinase assays as well as in the STAT6 and STAT5 assays. Results are disclosed in Table 1

TABLE 1

| Compound | JAK1 $EC_{50}$ (nM) | JAK2 $EC_{50}$ (nM) | JAK3 $EC_{50}$ (nM) | TYK2 $EC_{50}$ (nM) | STAT6 $EC_{50}$ (nM) | STAT5 $EC_{50}$ (nM) | JAK2/JAK1 ratio | JAK3/JAK1 ratio | STAT6/STAT5 ratio |
|---|---|---|---|---|---|---|---|---|---|
| Example 1 | 10.8 | 530 | 5260 | 111 | 237 | 14600 | 49 | 487 | 62 |
| Example 2 | 44.4 | 1130 | 9820 | 466 | 1160 | >42600 | 25 | 221 | >37 |
| Example 3 | 3.48 | 171 | 1700 | 32.0 | 94.5 | 6420 | 51 | 489 | 68 |
| Example 4 | 3.46 | 153 | 2310 | 43.0 | 141 | 7080 | 44 | 668 | 50 |
| Example 5 | 8.41 | 301 | 3200 | 102 | 270 | 9240 | 36 | 380 | 34 |
| Example 6 | 508 | 2640 | 2870 | 1110 | 8570 | >49800 | 5.2 | 5.6 | >5.8 |
| Example 7 | 129 | 981 | 1010 | 443 | 3460 | >49800 | 7.6 | 7.8 | >14 |
| Example 644* of WO2011086053 | 0.34 | 3.34 | 13.1 | 3.32 | 10.5 | 123 | 9.8 | 39 | 12 |
| Example 641* of WO2011086053 | 6.81 | 228 | 739 | 115 | 178 | 5740 | 33 | 109 | 32 |

*Example 641 and Example 644 of WO2011086053 were prepared according to WO2011086053

The selectivity for JAK1 over JAK2 or JAK3 is calculated as JAK2:JAK1 or JAK3:JAK1 ratio of the respective $EC_{50}$. Similar calculation is done for the selectivity for STAT6 over STAT5. As can be seen from Table 1 compounds of the present invention show a high selectivity for JAK1 inhibition over JAK2 and JAK3; and a high selectivity for STAT6 inhibition (reflecting JAK1 inhibition) over STAT5 (reflecting JAK2 inhibition).

Kinase Selectivity

The kinase selectivity profiles of Example 3 of the present invention as well as Examples 644 and 641 of WO2011086053 were evaluated at CARNA Biosciences Inc. with a panel consisting of 23 Tyrosine kinases, including JAK1 (ABL, CSK, EGFR, EPHA2, EPHB1, EPHB4, FGFR1, FLT3, IGF1R, ITK, JAK1, JAK3, KDR, LCK, MET, PDGFRα, PDGFRβ, PYK2, SRC, TIE2, TRKA and TYRO3) as well as 68 Serine and Threonine kinases (LCK, MET, AKT1, AMPKα1/β1/γ1, AurA, AurB, AurC, BRSK2 ([ATP]=Km value), CaMK1a ([ATP]=Km value), CaMK2a ([ATP]=Km value), CaMK4, CDC2/CycB1, CDC7/ASK, CDK2/CycA2, CDK2/CyE1, CDK3/CyE1 ([ATP]=Km value), CDK4/CyD3, CDK6/CyD3, CDK7/CycH/MAT1, CDK9/CycT1, CHK1, CK1ε, CK2α1/β, CK2α2/β, CLK1, CLK2, DAPK1, DYRK1B, Erk2, GSK3α, GSK3β, HGK, IKKβ, IRAK4 ([ATP]=Km value), JNK2, LOK ([ATP]=Km value), MAPKAP2, MLK1, MLK2, MNK2 ([ATP]=Km value), MST1, MST2 ([ATP]=Km value), NEK1, NEK2, NEK6, NEK7, NEK9, p38α, p70S6K, PAK1 ([ATP]=Km value), PAK2, PAK5 ([ATP]=Km value), PBK, PDK1, PIM1, PIM2, PKACα, PKCα, OKD2, PKN1 ([ATP]=Km value), PLK1, PLK2 ([ATP]=Km value), ROCK1, RSK1, SGK, skMLCK ([ATP]=Km value) and TSSK1). The evaluation was generally conducted at an ATP concentration of 1 mM, however for certain kinases ATP concentrations close to the corresponding Km-values were used (this is stated in brackets at each of the relevant kinases). The percentage of inhibition was measured at an inhibitor concentration of approximately 1000 times JAK1 $EC_{50}$. The results are summarized in Table 2:

TABLE 2

| | Example 3 (4 μM) | Example 644 of WO2011086053 (0.4 μM) | Example 641 of WO2011086053 (9 μM) |
|---|---|---|---|
| | 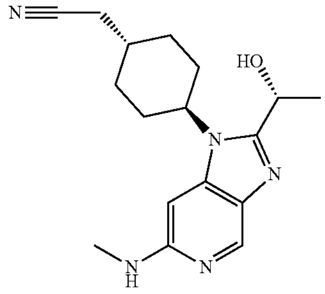 | 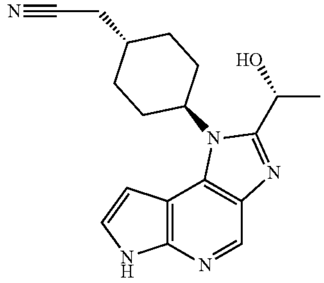 | 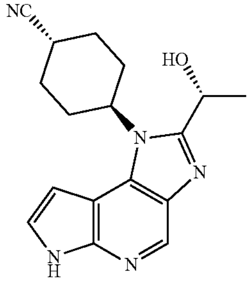 |
| Tyrosine kinases inhibited by 50% or more at an ATP concentration of 1 mM (n ≥ 2) | JAK1 | JAK1<br>FGFR1<br>FLT3<br>KDR<br>PDGFRα<br>PDGFRβ | JAK1<br>FGFR1<br>FLT3<br>KDR<br>PDGFRα |
| Serine and Threonine kinases inhibited by 50% or more (n ≥ 2) | | BRSK2, [ATP] = 50 μM<br>LOK, [ATP] = 100 μM<br>MST2, [ATP] = 75 μM<br>PKN1, [ATP] = 25 μM | BRSK2, [ATP] = 50 μM<br>LOK, [ATP] = 100 μM<br>MST1, [ATP] = 1 mM<br>MST2, [ATP] = 75 μM<br>PKN1, [ATP] = 25 μM |

As shown in Table 2, Example 3 of the present invention displayed a very high level of selectivity towards a large panel of kinases; i.e. none of the tested kinases except JAK1 were inhibited by more than 50%.

Examples 644 and 641 of WO2011086053 inhibited nine other kinases besides JAK1 by 50% or more.

Inhibition of off-target kinases increases the risk of adverse effects, i.e. a high kinase selectivity may reduce the risk of adverse effects.

CYP Inhibition and CYP Induction

Reversible CYP inhibition, time dependent CYP inhibition (TDI) and CYP induction was tested at Cyprotex PLC according to authority guidance.

For reversible CYP inhibition the IC50 was measured up to a substrate concentration of 50 μM for Example 3 and up to 25 μM for Examples 644 and 641 of WO2011086053.

The reversible CYP inhibition results are summarized in Table 3.

TABLE 3

| | 1A2 IC50 (μM) | 2B6 IC50 (μM) | 2C8 IC50 (μM) | 2C9 IC50 (μM) | 2C19 IC50 (μM) | 2D6 IC50 (μM) | 3A4 IC50 (μM) |
|---|---|---|---|---|---|---|---|
| Example 3 | >50 | >50 | >50 | >50 | >50 | >50 | >50 |
| Example 644 of WO2011086053 | >25 | ND | ND | >25 | >25 | >25 | 10.8 |

TABLE 3-continued

| | 1A2 IC50 (μM) | 2B6 IC50 (μM) | 2C8 IC50 (μM) | 2C9 IC50 (μM) | 2C19 IC50 (μM) | 2D6 IC50 (μM) | 3A4 IC50 (μM) |
|---|---|---|---|---|---|---|---|
| Example 641 of WO2011086053 | >25 | ND | ND | >25 | >25 | >25 | 10.9 |

ND = Not determined

As can be seen from Table 3, Example 3 displays no CYP inhibition when measured at substrate concentrations up to 50 μM.

Examples 644 and 641 of WO2011086053 indicate weak CYP3A4 inhibition.

No time dependent CYP inhibition was indicated for Example 3.

CYP3A4 inhibition may indicate undesirable drug-drug interactions. CYP inhibition may affect the plasma levels and increase the exposure of co-administered drugs and potentially lead to adverse drug reactions or toxicity.

Induction of CYP1A2, CYP2B6 and CYP3A4 gene expression can serve as sensitive representative endpoints for activation of aryl hydrocarbon receptor (AhR), pregnane X receptor (PXR) and constitutive androstane receptor (CAR), respectively. Induction of these nuclear receptors was assessed by measuring the increase in mRNA encoding for AhR, CAR, and PXR, respectively, at relevant concentrations.

A >2-fold shift indicate CYP Induction.

The results from the three highest incubation concentrations are summarized in Table 4.

TABLE 4

| | Mean fold shift compared to vehicle in CYP induction | | |
|---|---|---|---|
| | Fold shift in mRNA expr. (CYP 1A2) | Fold shift in mRNA expr. (CYP 2B6) | Fold shift in mRNA expr. (CYP 3A4) |
| Example 3 | 0.8 (@ 0.1 μM)<br>0.7 (@ 1.0 μM)<br>0.8 (@ 10 μM) | 1.1 (@ 0.1 μM)<br>1.5 (@ 1.0 μM)<br>1.7 (@10 μM) | 1.2 (@ 5.0 μM)<br>1.5 (@ 20 μM)<br>2.0 (@ 50 μM) |

TABLE 4-continued

| Mean fold shift compared to vehicle in CYP induction | | | |
|---|---|---|---|
| | Fold shift in mRNA expr. (CYP 1A2) | Fold shift in mRNA expr. (CYP 2B6) | Fold shift in mRNA expr. (CYP 3A4) |
| Example 644 of WO2011086053 | 0.8 (@ 0.1 μM) | 1.3 (@ 0.1 μM) | 1.3 (@ 0.1 μM) |
| | 0.8 (@ 1.0 μM) | 2.0 (@ 1.0 μM) | 1.4 (@ 1.0 μM) |
| | 1.6 (@ 10 μM) | 7.3 (@10 μM) | 5.4 (@ 10 μM) |
| Example 641 of WO2011086053 | 0.9 (@ 0.1 μM) | 1.0 (@ 0.1 μM) | 1.8 (@ 5.0 μM) |
| | 0.8 (@ 1.0 μM) | 1.3 (@ 1.0 μM) | 2.5 (@ 20 μM) |
| | 0.9 (@ 10 μM) | 1.4 (@10 μM) | 4.0 (@ 50 μM) |

As can be seen from Table 4, Example 3 does not cause CYP3A4 induction up to at least a concentration of 50 μM or CYP1A2 and CYP2B6 induction up to at least a concentration of 10 μM Example 644 of WO2011086053 causes CYP3A4 induction at a concentration of 10 μM and CYP2B6 induction at a concentration of 10 μM, and Example 641 of WO2011086053 causes CYP3A4 induction at a concentration of 20 μM and above.

CYP3A4 induction may indicate undesirable drug-drug interactions. CYP induction may reduce the exposure of co-administered drugs resulting in a decrease in efficacy. In addition, CYP induction can also lead to toxicity by increasing reactive metabolite formation.

Aqueous Solubility of Crystalline Material

The aqueous solubility of crystalline Example 3, Example 644 and 641 of WO2011086053 at different pH's was evaluated. The solubility in mg/mL are summarized in Table 5:

TABLE 5

| | Example 3 [crystalline form, m.p. (DSC onset temperature) 143 ± 2° C.] Solubility (mg/mL) | Example 644 of WO2011086053 [crystalline form, m.p. (DSC onset temperature) 244 ± 2° C.] Solubility (mg/mL) | Example 641 of WO2011086053 [mix of two crystalline forms, m.p. (DSC onset temperature) 188 ± 2 and 195 ± 2° C.] Solubility (mg/mL) |
|---|---|---|---|
| pH 2.0 | >346 | 2.47 | 90.0 |
| pH 7.4 | 12.3 | 0.136 | 2.26 |
| pH 9.0 | 11.1 | 0.0099 | 2.28 |

In general, aqueous solubility is one of the key aspects affecting the development of oral formulations and oral bioavailability is highly dependent on the solubility of a drug. A high solubility will drive a fast dissolution of the compound in the GI tract and the high concentrations reached will drive absorption across the intestinal epithelium. Hence, a high solubility may significantly increase the likelihood of achieving a high oral bioavailability and desired systemic exposures at relevant doses.

The invention claimed is:

1. A compound according to general formula (I)

(I)

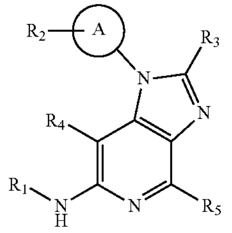

wherein

A represents $C_6$-cycloalkyl, wherein said $C_6$-cycloalkyl is optionally substituted with one or more deuterium;

$R_1$ represents $C_1$-alkyl, wherein said $C_1$-alkyl is optionally substituted with one or more deuterium;

$R_2$ represents $C_1$-alkyl, wherein said $C_1$-alkyl is substituted with a $R_6$, and wherein said $C_1$-alkyl is optionally substituted with one or more deuterium;

$R_3$ represents $C_2$-alkyl, wherein said $C_2$-alkyl is substituted with a $R_7$, and wherein said $C_2$-alkyl is optionally substituted with one or more deuterium;

$R_4$ represents hydrogen or deuterium;

$R_5$ represents hydrogen or deuterium;

$R_6$ represents cyano; and $R_7$ represents hydroxyl;

or a pharmaceutically acceptable salt, hydrate or solvate thereof.

2. The compound according to claim 1 wherein formula (I) is general formula (Ia)

(Ia)

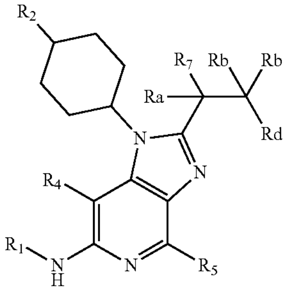

wherein Ra, Rb, Rc, and Rd each independently are selected from hydrogen and deuterium.

3. The compound according to claim 1 wherein formula (I) is general formula (Ib)

(Ib)

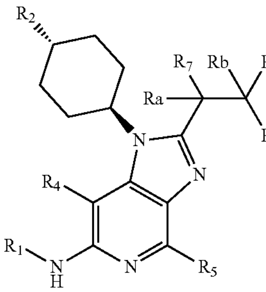

wherein Ra, Rb, Rc, and Rd each independently are selected from hydrogen and deuterium.

4. The compound according to claim 1 wherein said compound is selected from (i) trans-2-[4-[2-[1-Hydroxyethyl]-6-(methylamino)imidazo[4,5-c]pyridin-1-yl]cyclohexyl]acetonitrile, (ii) trans-2-[4-[2-[(1 S)-1-Hydroxyethyl]-6-(methylamino)imidazo[4,5-c]pyridin-1-yl]cyclohexyl]acetonitrile, (iii) trans-2-[4-[2-[(1R)-1-Hydroxyethyl]-6-(methylamino)imidazo[4,5-c]pyridin-1-yl]cyclohexyl]acetonitrile, (iv) trans-2-[4-[2-[(1R)-1-Hydroxyethyl]-6-(trideuteriomethylamino)imidazo[4,5-c]pyridin-1-yl]cyclohexyl] acetonitrile, (v) trans-2-[4-[2-[1,2,2,2-Tetradeuterio-1-hydroxyethyl]-6-(methylamino)imidazo[4,5-c]pyridin-1-yl]cyclohexyl]acetonitrile, (vi) cis-2-[4-[2-[1-Hydroxyethyl]-6-(methylamino)imidazo[4,5-c]pyridin-1-yl]cyclohexyl]acetonitrile, and (vii) cis-2-[4-[2-[(1R)-1-Hydroxyethyl]-6-(methylamino) imidazo[4,5-c]pyridin-1-yl]cyclohexyl]acetonitrile, or a pharmaceutically acceptable salt, hydrate or solvate thereof.

5. The compound according to claim 1 wherein said compound is trans-2-[4-[2-[(1R)-1-Hydroxyethyl]-6-(methyl-amino)-imidazo[4,5-c]pyridin-1-yl]cyclohexyl]acetonitrile, or a pharmaceutically acceptable salt, hydrate, or solvate thereof.

6. The compound

2-[trans-4-[(5-Amino-2-chloropyridin-4-yl)amino]cyclohexyl]acetonitrile or a pharmaceutically acceptable salt hydrate, or solvate thereof.

7. A compound selected from (i) 2-[trans-4-[6-Chloro-2-(1-hydroxyethyl)-1H-imidazo [4,5-c]pyridin-1-yl]cyclo-hexyl]-acetonitrile, (ii) 2-[trans-4-[6-Chloro-2-[(1R)-1-hydroxyethyl]-1H-imidazo[4,5-c]pyridin-1-yl]cyclohexyl]acetonitrile, and (iii) trans-2-[4-[6-Chloro-2-(1,2,2,2-tetradeuterio-1-hydroxy-ethyl)imidazo[4,5-c]pyridin-1-yl]cyclohexyl] acetonitrile, or a pharmaceutically acceptable salt, hydrate, or solvate thereof.

8. A pharmaceutical composition comprising a compound according to claim 1 and one or more pharmaceutically acceptable vehicles or excipients and/or pharmaceutically acceptable carriers.

9. The pharmaceutical composition according to claim 8, together with one or more other therapeutically active compounds.

10. A method of treating or ameliorating one or more diseases of the immune system comprising administering to a person suffering from at least one of said diseases an effective amount of one or more compounds according to claim 1.

11. The method of claim 10, wherein the disease is related to the deregulation of the immune system.

12. The method of claim 1, wherein the disease is atopic dermatitis.

13. The method of claim 10, wherein the disease is responsive to the inhibition of JAK1 kinase activity.

14. A method of treating or ameliorating one or more diseases of the immune system, comprising administering to a person suffering from at least one of said diseases an effective amount of the pharmaceutical composition according to claim 8.

* * * * *

UNITED STATES PATENT AND TRADEMARK OFFICE

CERTIFICATE OF CORRECTION

PATENT NO. : 10,703,751 B2
APPLICATION NO. : 16/477249
DATED : July 7, 2020
INVENTOR(S) : Jens Larsen et al.

It is certified that error appears in the above-identified patent and that said Letters Patent is hereby corrected as shown below:

On the Title Page

Item (72), in the Inventors, Lines 1-2, “Mogens Larsen, Ballerup (GB);” should read --Mogens Larsen, Ballerup (DK);--.

Item (57), in the Abstract, Lines 9-10, “treatment autoimmune diseases” should read --treatment of autoimmune diseases--.

In the Claims

In Claim 1, Column 56, Line 36, “with a $R_6$,” should read --with $R_6$,--.

In Claim 1, Column 56, Line 39, “with a $R_7$,” should read --with $R_7$,--.

In Claim 2, Column 56, Lines 52-64, in the chemical structure for formula (Ia):

(Ia)

“ 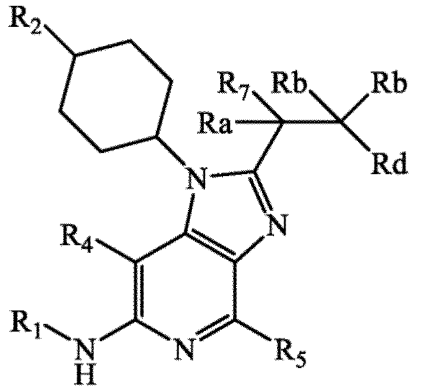 ”

Signed and Sealed this
Thirty-first Day of January, 2023

Katherine Kelly Vidal
*Director of the United States Patent and Trademark Office*

Should read:

(Ia)

-- 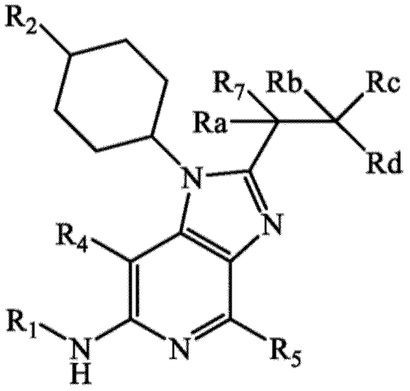 --.

In Claim 3, Column 57, Lines 5-16, in the chemical structure for formula (Ib):

(Ib)

“ 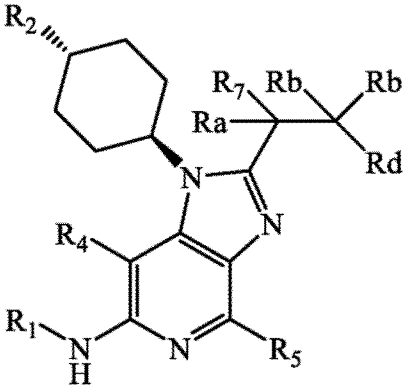 ”

Should read:

(Ib)

-- 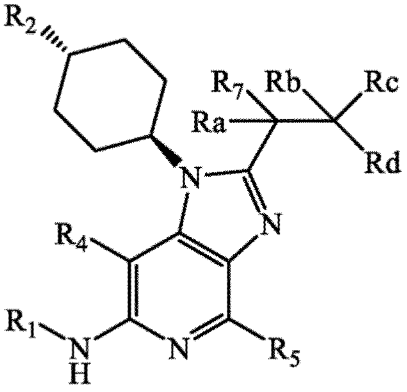 --.

In Claim 6, Column 58, Line 10, “salt hydrate, or solvate” should read --salt, hydrate, or solvate--.

In Claim 9, Column 58, Lines 26-27, “according to claim 8, together” should read --according to claim 8 together--.

In Claim 10, Column 58, Line 30, “immune system comprising” should read --immune system, comprising--.

In Claim 12, Column 58, Line 35, "method of claim 1," should read --method of claim 10,--.